(12) United States Patent
Hoegerle et al.

(10) Patent No.: US 9,101,337 B2
(45) Date of Patent: Aug. 11, 2015

(54) SURGICAL COUPLING SYSTEM AND SURGICAL DRIVE SYSTEM

(71) Applicant: Aesculap AG, Tuttlingen (DE)

(72) Inventors: Roland Hoegerle, Tuttlingen (DE); Martin Machill, Rietheim-Weilheim (DE); Ralf Pfister, Trossingen (DE)

(73) Assignee: Aesculap AG, Tuttlingen (DE)

( * ) Notice: Subject to any disclaimer, the term of this patent is extended or adjusted under 35 U.S.C. 154(b) by 37 days.

(21) Appl. No.: 14/048,133

(22) Filed: Oct. 8, 2013

(65) Prior Publication Data

US 2014/0051304 A1 Feb. 20, 2014

Related U.S. Application Data

(63) Continuation of application No. PCT/EP2012/057918, filed on Apr. 30, 2012.

(30) Foreign Application Priority Data

May 6, 2011 (DE) .......................... 10 2011 050 192

(51) Int. Cl.
*A61B 17/00* (2006.01)
*A61B 17/16* (2006.01)
(Continued)

(52) U.S. Cl.
CPC .............. *A61B 17/00* (2013.01); *A61B 17/1622* (2013.01); *A61B 17/1624* (2013.01); *A61B 17/1626* (2013.01); *A61C 1/185* (2013.01); *A61B 17/1628* (2013.01); *A61B 2017/0003* (2013.01); *A61B 2017/00199* (2013.01); *A61B 2017/00212* (2013.01); *A61B 2017/00221* (2013.01);
(Continued)

(58) Field of Classification Search
CPC ........... H01R 13/6272; H01R 13/6275; H01R 23/7068
USPC .............. 200/515, 318, 51.09, 320, 321, 323, 200/325
See application file for complete search history.

(56) References Cited

U.S. PATENT DOCUMENTS 5,176,528 A * 1/1993 Fry et al. ........................ 439/181
6,017,354 A * 1/2000 Culp et al. ..................... 606/170
(Continued)

FOREIGN PATENT DOCUMENTS

DE  102 25 857  1/2004
DE  10 2006 051 511  5/2008
(Continued)

*Primary Examiner* — Gary Paumen
(74) *Attorney, Agent, or Firm* — Lipsitz & McAllister, LLC

(57) ABSTRACT

The invention relates to a surgical coupling system which comprises first and second surgical coupling devices each having at least two electrical coupling contacts that are moveable mechanically into engagement with one another. The coupling devices are completely separated from each other in a separated position and are mechanically in engagement with one another in a mechanical coupling position. The system further comprises an electrical switching device which, in the coupling position, is moveable from an OFF position, in which at least one first electrical coupling contact of the first coupling device and at least one first electrical coupling contact of the second coupling device are out of engagement, into an ON position in which the at least one first electrical coupling contact of the first coupling device and the at least one first electrical coupling contact of the second coupling device are in electrically conductive contact or engagement.

24 Claims, 24 Drawing Sheets

Figure 1:
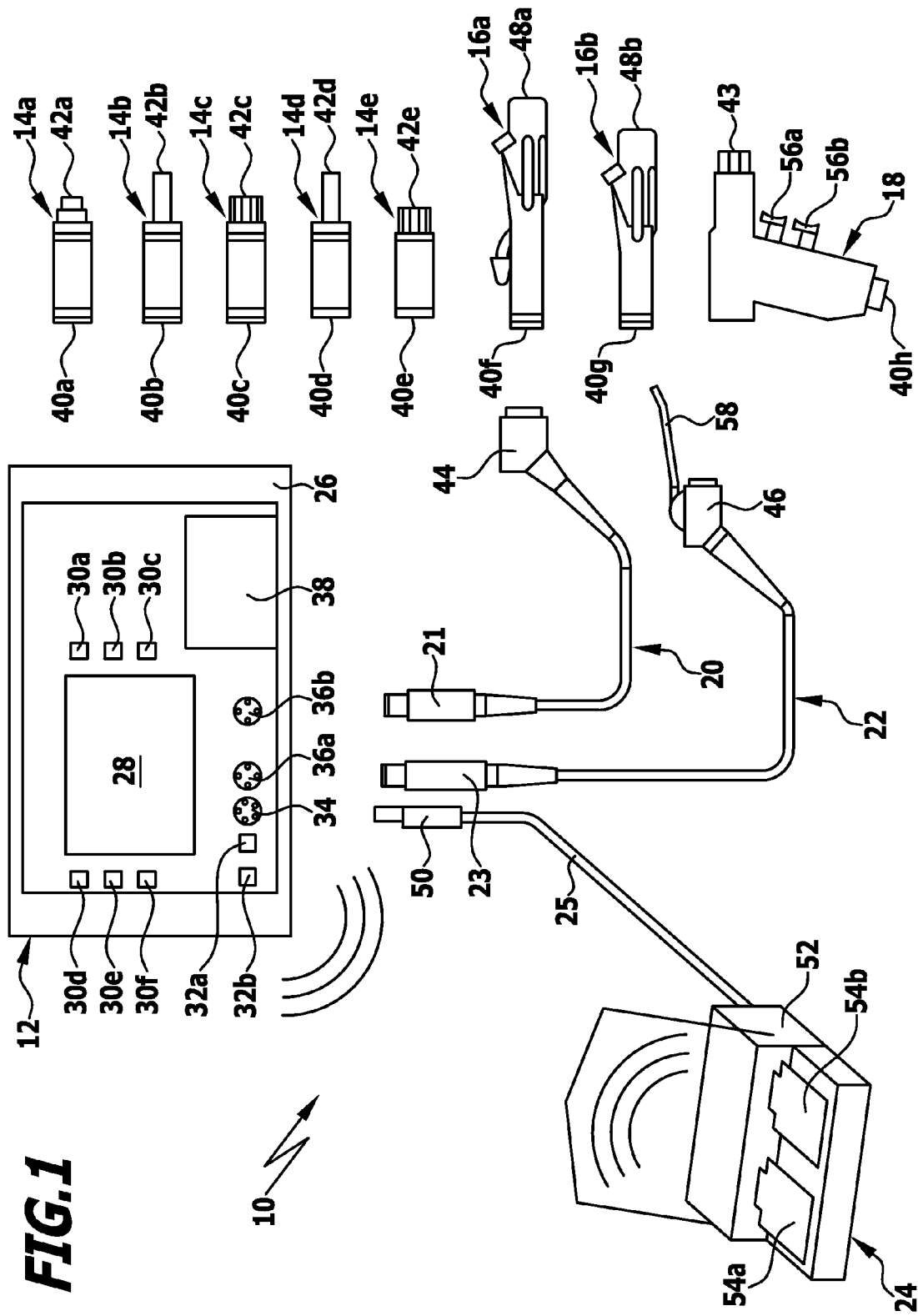

(51) Int. Cl.
    *A61C 1/18*     (2006.01)
    *A61B 19/00*     (2006.01)

(52) U.S. Cl.
    CPC ............ *A61B2017/00398* (2013.01); *A61B 2017/00464* (2013.01); *A61B 2017/00482* (2013.01); *A61B 2017/00973* (2013.01); *A61B 2019/304* (2013.01); *A61B 2019/448* (2013.01)

(56) References Cited

U.S. PATENT DOCUMENTS

| | | | |
|---|---|---|---|
| 6,090,123 | A | 7/2000 | Culp et al. |
| 6,329,778 | B1 * | 12/2001 | Culp et al. .................. 318/434 |
| 6,338,657 | B1 * | 1/2002 | Harper et al. ............... 439/692 |
| 6,447,340 | B1 * | 9/2002 | Wu ............................... 439/660 |
| 6,555,773 | B1 * | 4/2003 | Broghammer et al. .... 200/61.85 |
| 6,752,816 | B2 | 6/2004 | Culp et al. |
| 6,958,455 | B1 * | 10/2005 | Lui ............................. 200/43.17 |
| 7,217,150 | B2 * | 5/2007 | Lekic et al. .................. 439/352 |
| 7,435,112 | B1 | 10/2008 | Miller et al. |
| 7,494,363 | B1 * | 2/2009 | Wu .............................. 439/352 |
| 7,517,351 | B2 | 4/2009 | Culp et al. |
| 7,914,315 | B2 | 3/2011 | Kuhn et al. |
| 7,934,939 | B2 * | 5/2011 | Chen et al. .................. 439/352 |
| 7,998,157 | B2 | 8/2011 | Culp et al. |
| 8,395,062 | B2 * | 3/2013 | Suzuki ........................ 200/16 R |
| 2002/0087179 | A1 * | 7/2002 | Culp et al. .................. 606/167 |
| 2004/0225310 | A1 * | 11/2004 | Culp et al. .................. 606/170 |
| 2008/0114388 | A1 | 5/2008 | Culp et al. |
| 2009/0099423 | A1 | 4/2009 | Al-Ali et al. |
| 2010/0221676 | A1 * | 9/2010 | Kuhn et al. .................. 433/29 |
| 2011/0266124 | A1 * | 11/2011 | Culp et al. .................. 200/335 |

FOREIGN PATENT DOCUMENTS

| | | |
|---|---|---|
| EP | 2 210 565 | 7/2010 |
| JP | 2002280119 | 9/2002 |

* cited by examiner

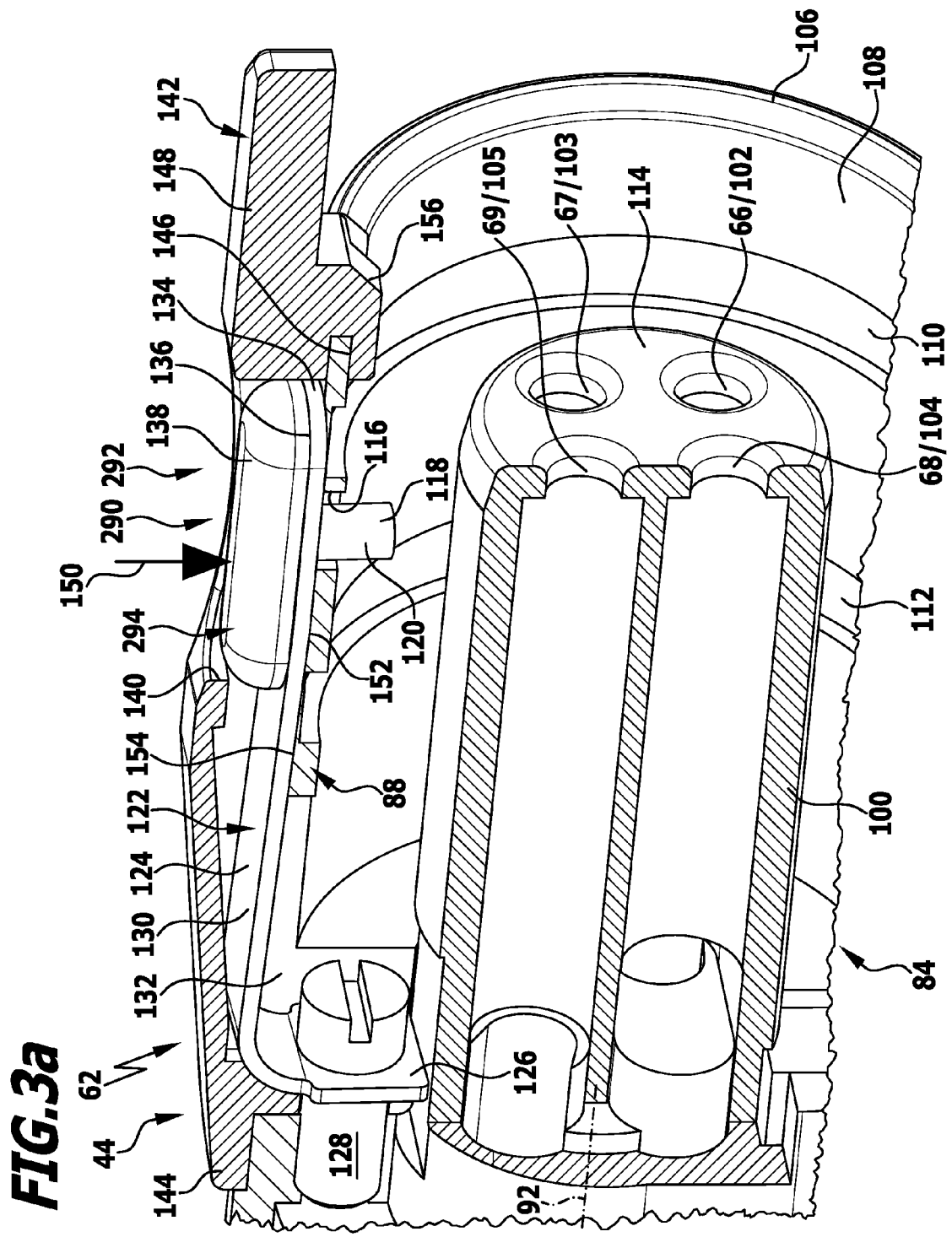

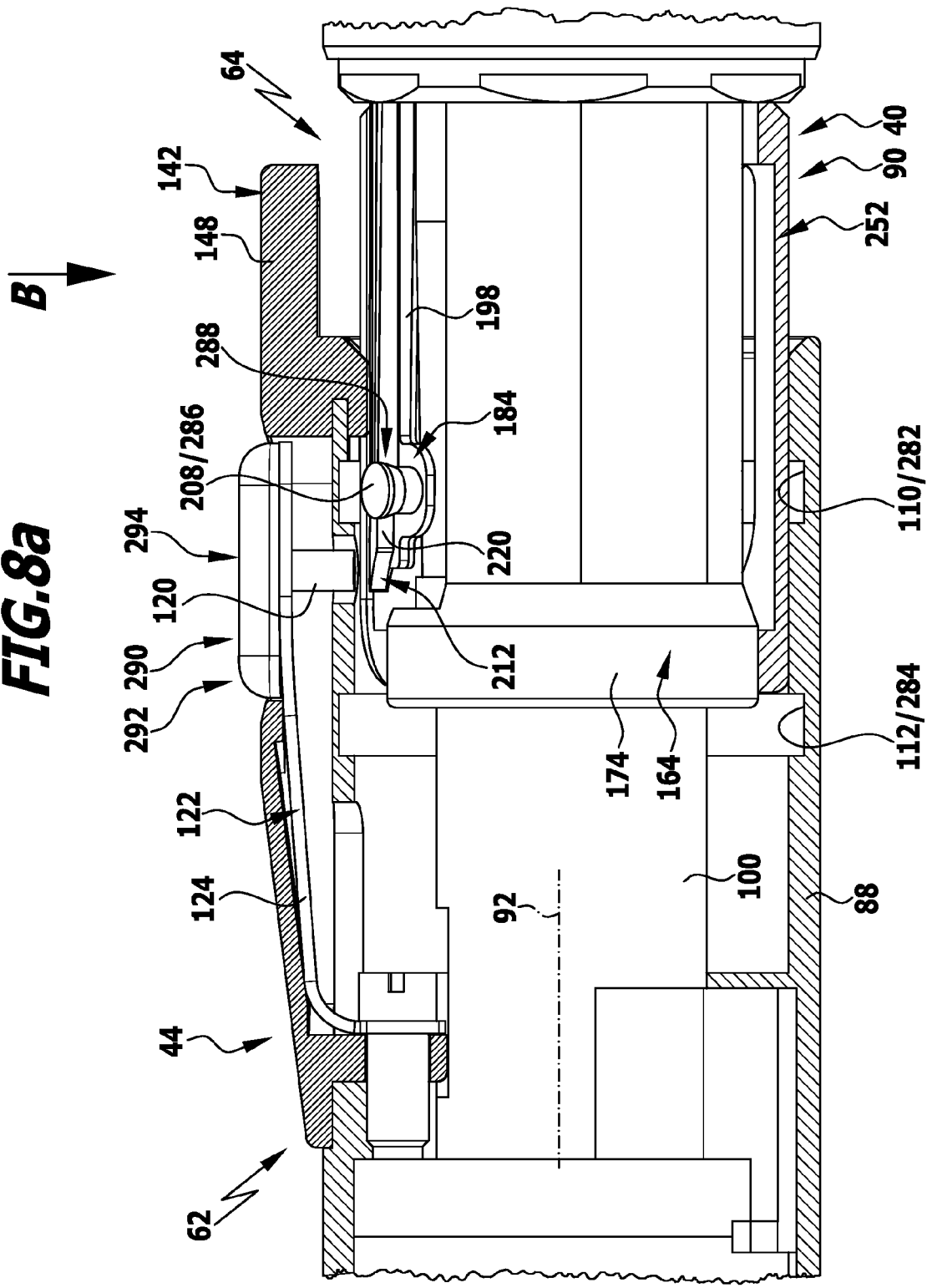

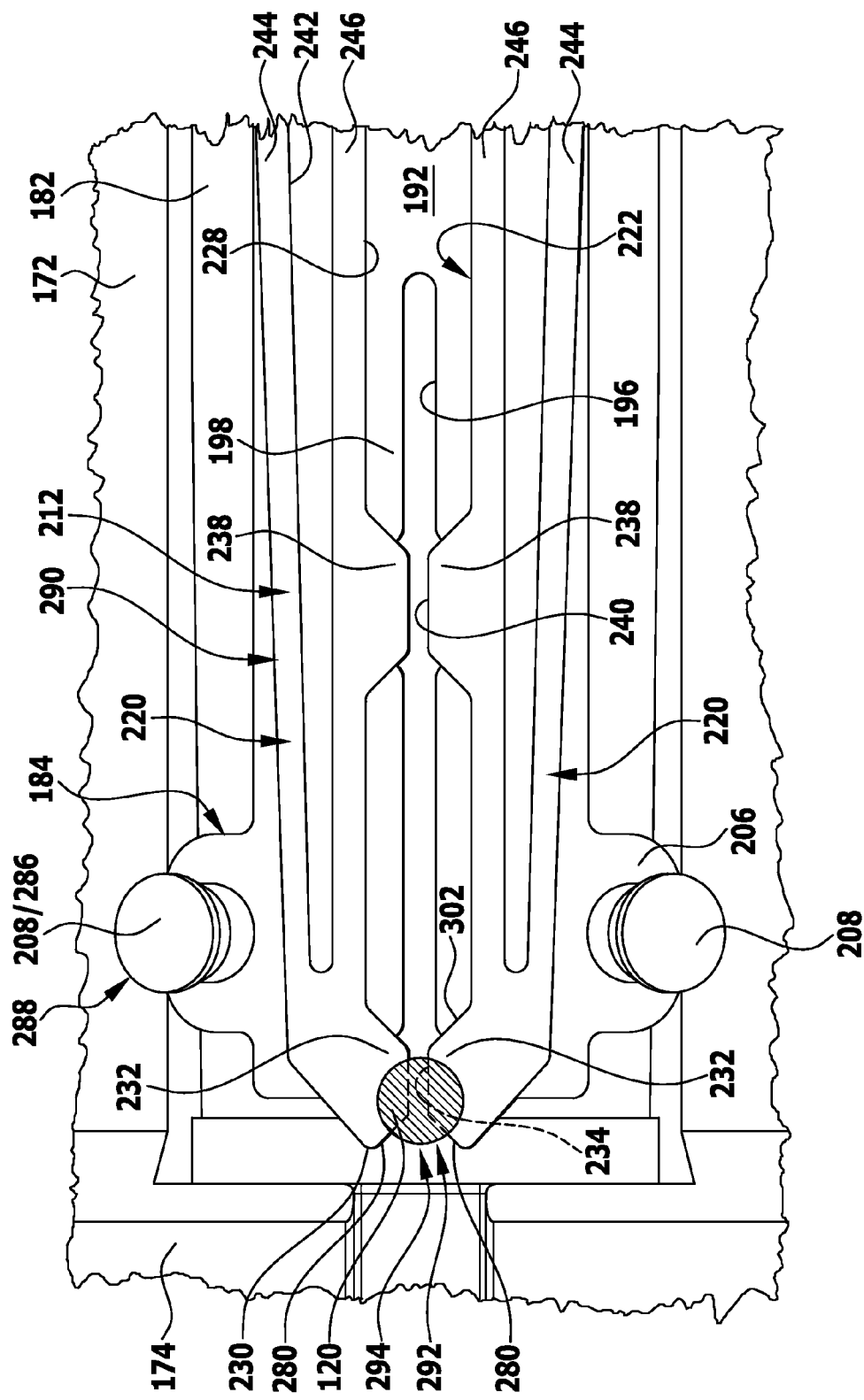

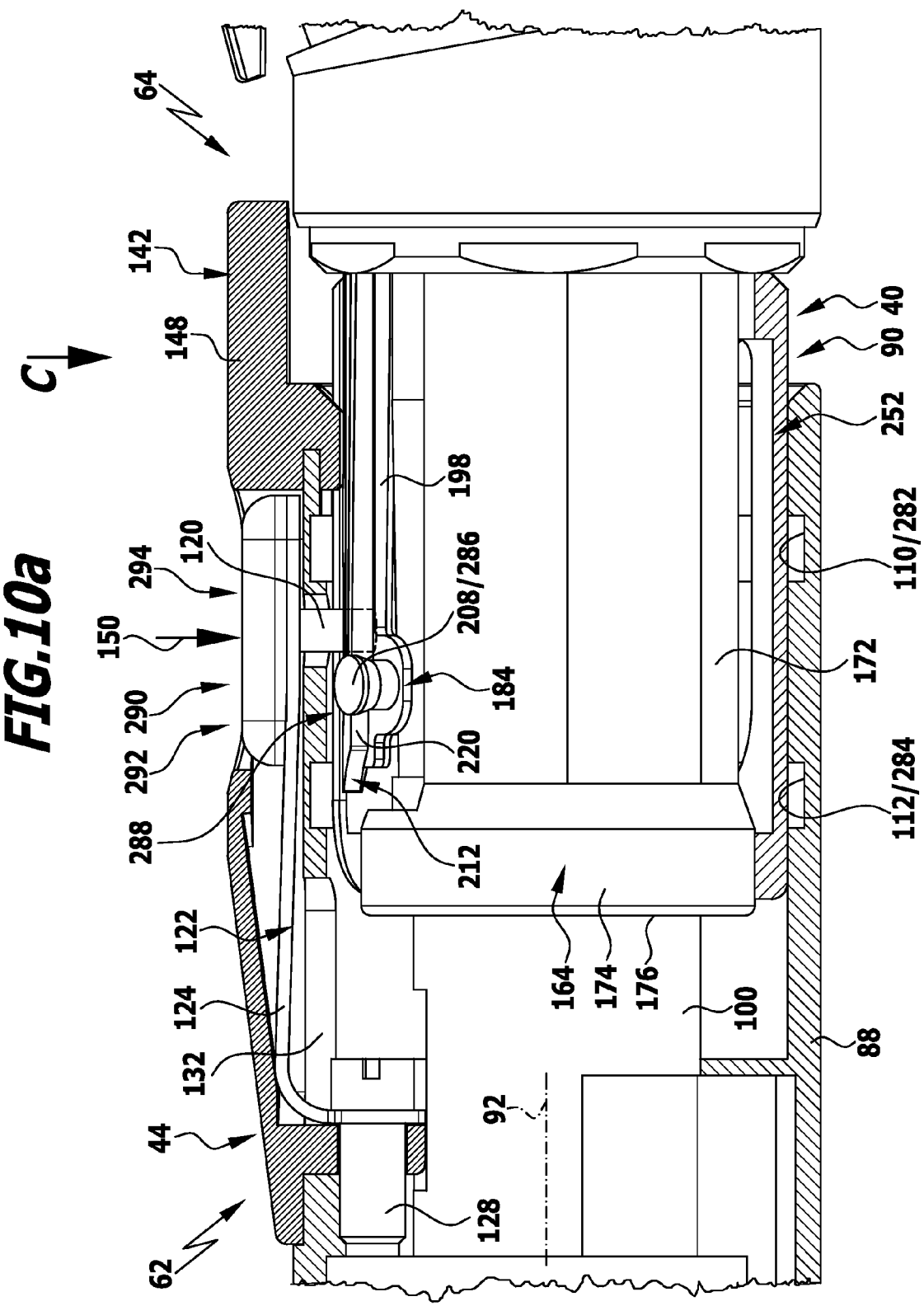

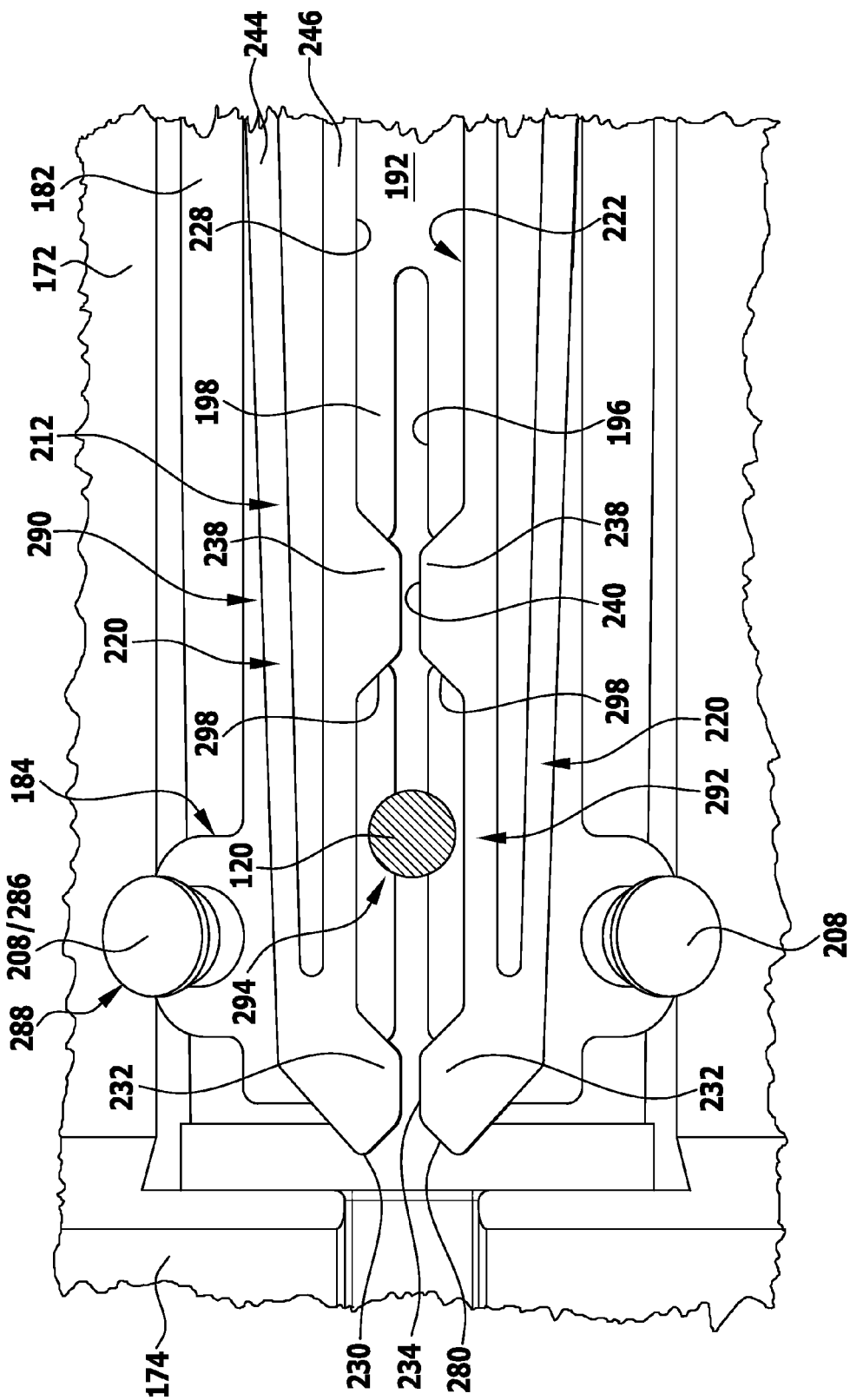

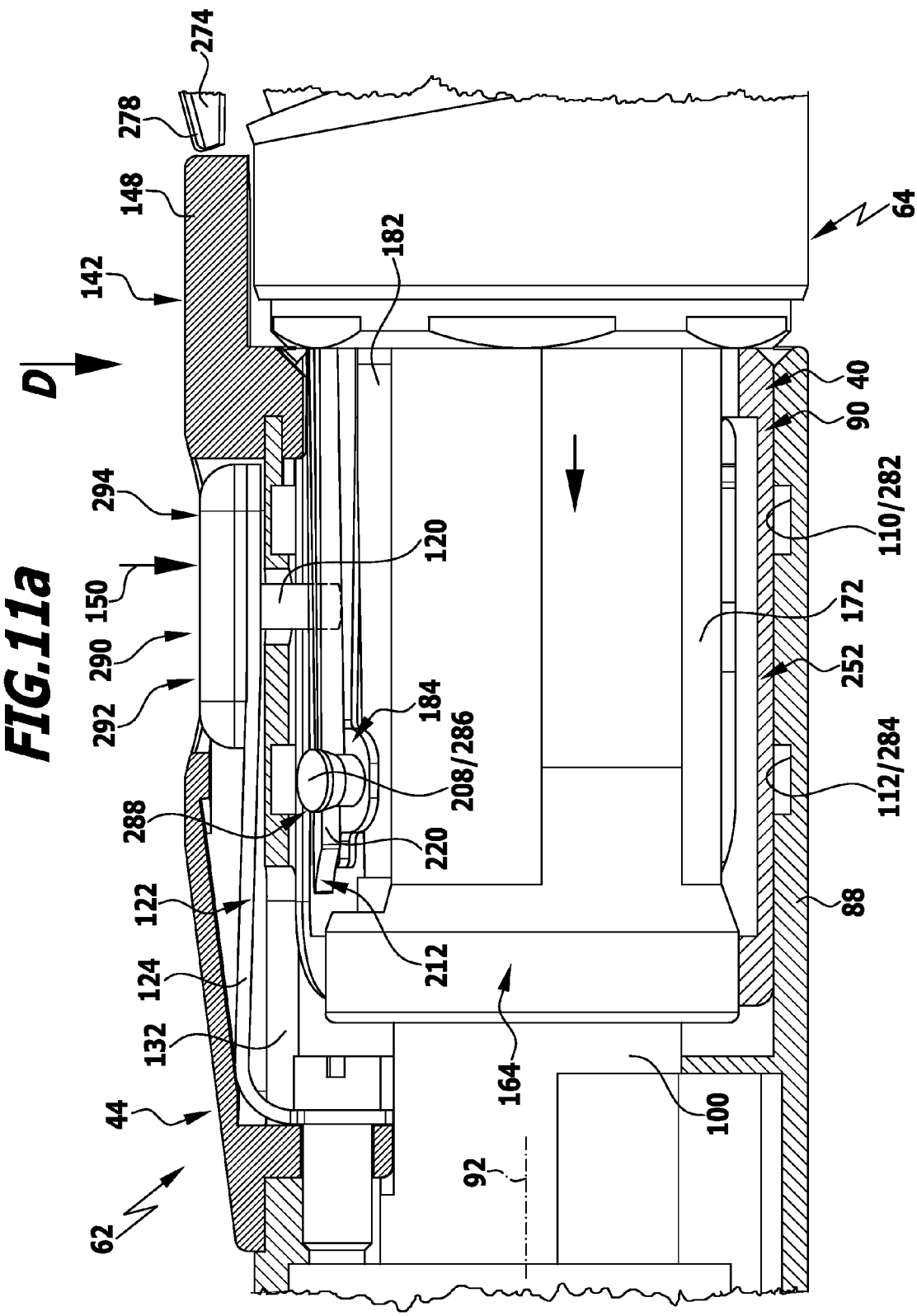

FIG.14
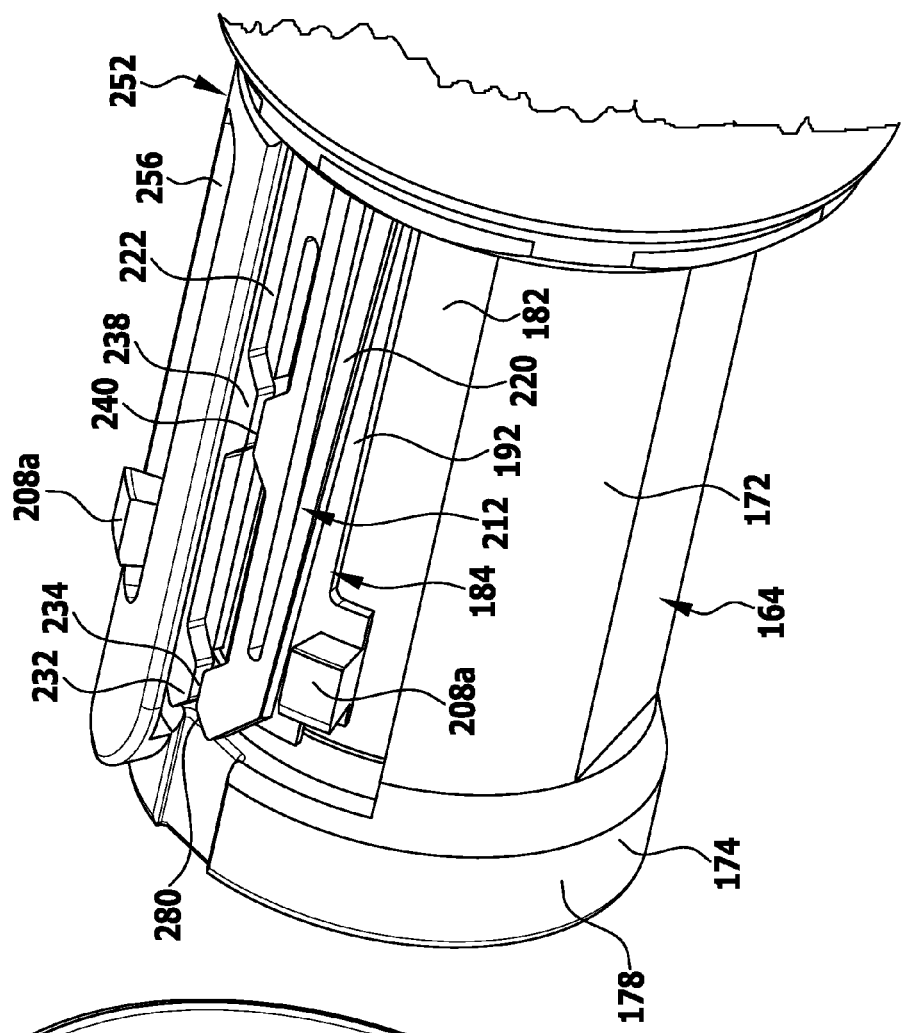
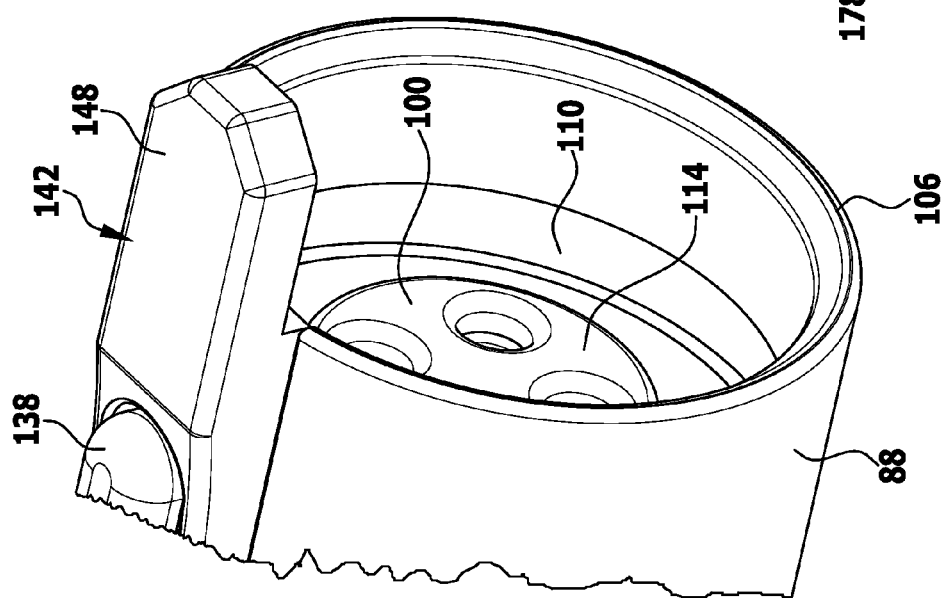

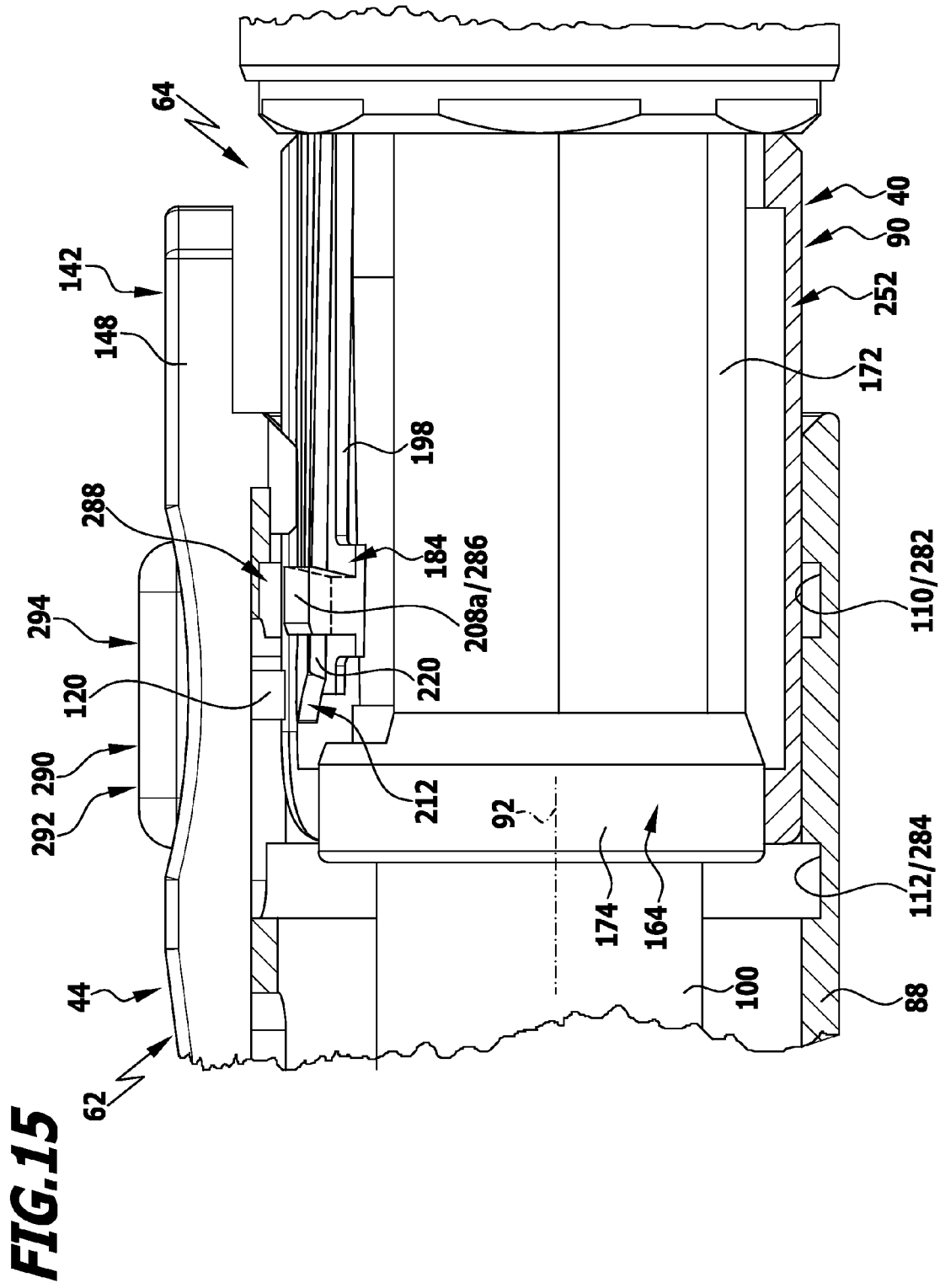

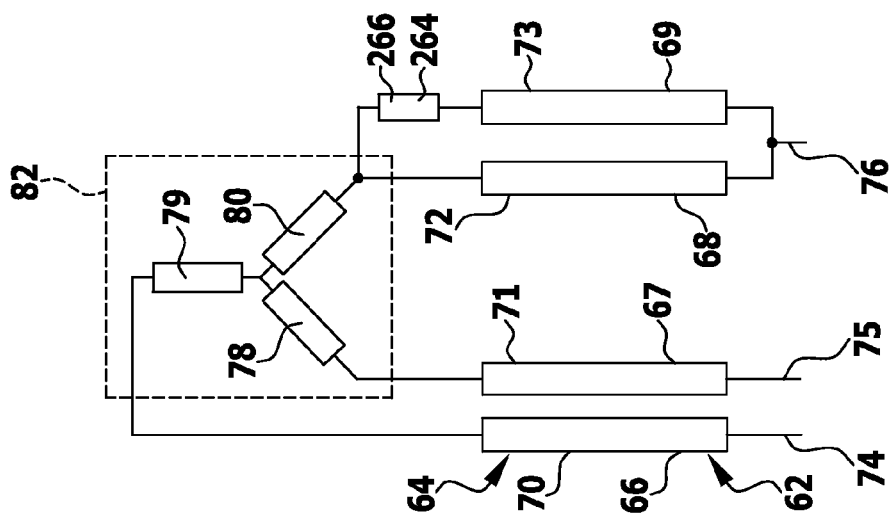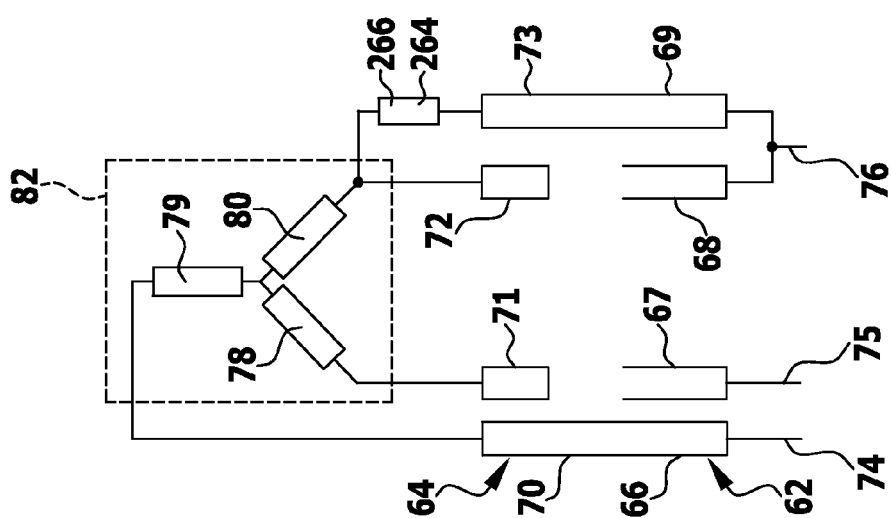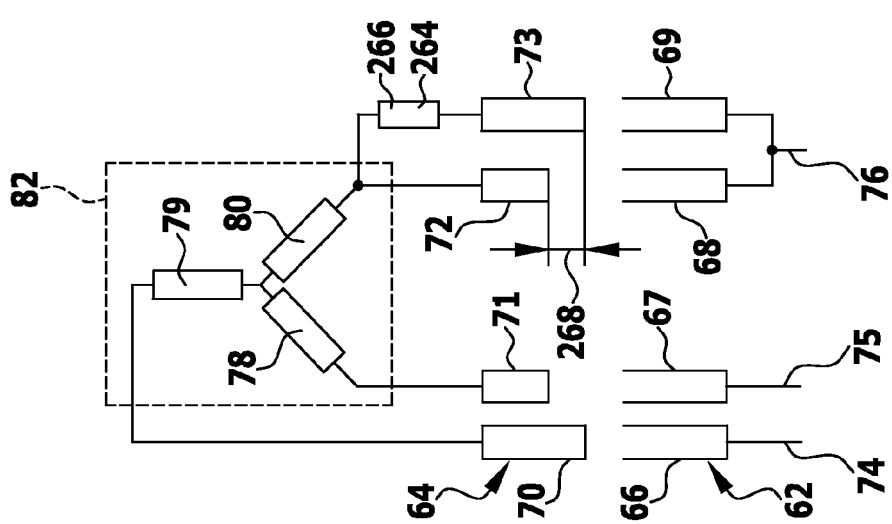

SURGICAL COUPLING SYSTEM AND SURGICAL DRIVE SYSTEM

CROSS-REFERENCE TO RELATED APPLICATIONS

This application is a continuation of international application number PCT/EP2012/057918 filed on Apr. 30, 2012 and claims the benefit of German application number 10 2011 050 192.4 filed on May 6, 2011, which are incorporated herein by reference in their entirety and for all purposes.

FIELD OF THE INVENTION

The present invention relates to a surgical coupling system generally, and more specifically to a surgical coupling system comprising a first surgical coupling device and a second surgical coupling device each of which comprises at least two electrical coupling contacts that are moveable into mechanical engagement with one another, wherein the first and the second coupling device are completely separated from each other in a separated position and are in mechanical engagement with one another in a mechanical coupling position.

Furthermore, the present invention relates to a surgical drive system generally, and more specifically to a surgical drive system comprising at least one surgical hand-piece having a drive in the form of an electric motor and at least one electrical supply line, which supply line comprises a first end that is releasably connectable to the at least one hand-piece and a second end that is releasably connectable to a control and/or regulating device for controlling and/or regulating the electric motor.

BACKGROUND OF THE INVENTION

A surgical coupling system and a surgical drive system of the type described hereinabove are known from DE 102 25 857 A1 for example. Surgical hand pieces incorporating an integrated drive in the form of an electric motor, also referred to hereinafter as surgical motorised hand pieces, are electrically coupled to the known drive system by means of a plug-type connection to a supply line which may also be referred to as a terminal cable. This plug connection process is effected in a sterile region in order to enable the hand pieces to be changed intra-operatively. This means however that the plug connection must be treated i.e. cleaned and sterilized after each usage. In particular thereby, the plug connections go through a superheated steam sterilization process.

For the purposes of activating the hand pieces, it is known to provide actuating elements such as hand switches for example on one of the two coupling devices of the coupling system, for example, on the coupling device provided on the terminal cable, or foot switches. If, in addition, there is a requirement for the type of hand-piece to be interrogated automatically by a control and/or regulating device of the drive system, also referred to simply as a motor control system hereinafter, then it is practically impossible to provide the terminal cable with only as many lines as the electric motor has windings, i.e. in the case of an electric motor comprising three motor windings, a terminal cable comprising just three lines. However, the provision of additional control or interrogating lines also means that the coupling system must have correspondingly more electrical terminal contacts. Since the hand pieces have to be treated again after each usage, this results in an undesirably high failure rate due to electrical contact problems in the case of present systems. And not just for the latter reason, but also because the switching elements presently being utilised for the activation of a motor current circuit are also susceptible to corrosion.

SUMMARY OF THE INVENTION

In a first aspect of the invention, a surgical coupling system comprises a first surgical coupling device and a second surgical coupling device each having at least two electrical coupling contacts that are moveable mechanically into engagement with one another. The first and the second coupling device are completely separated from each other in a separated position and are mechanically in engagement with one another in a mechanical coupling position. The surgical coupling system further comprises an electrical switching device which, in the coupling position, is moveable from an OFF position, in which at least one first electrical coupling contact of the first coupling device and at least one first electrical coupling contact of the second coupling device are out of engagement, into an ON position in which the at least one first electrical coupling contact of the first coupling device and the at least one first electrical coupling contact of the second coupling device are in electrically conductive contact or engagement, and/or vice versa.

In a second aspect of the invention, a surgical drive system comprises at least one surgical hand-piece having a drive in the form of an electric motor and at least one electrical supply line. Said supply line comprises a first end that is connectable to the at least one hand-piece in releasable manner and a second end that is connected or connectable in releasable manner to a control and/or regulating device for controlling and/or regulating the electric motor. The surgical drive system further comprises a coupling system for the electrical and mechanical connection of the hand-piece and the supply line. Said coupling system comprises a first surgical coupling device and a second surgical coupling device each having at least two electrical coupling contacts that are moveable mechanically into engagement with one another. The first and the second coupling device are completely separated from each other in a separated position and are mechanically in engagement with one another in a mechanical coupling position. The coupling system further comprises an electrical switching device which, in the coupling position, is moveable from an OFF position, in which at least one first electrical coupling contact of the first coupling device and at least one first electrical coupling contact of the second coupling device are out of engagement, into an ON position in which the at least one first electrical coupling contact of the first coupling device and the at least one first electrical coupling contact of the second coupling device are in electrically conductive contact or engagement, and/or vice versa.

BRIEF DESCRIPTION OF THE DRAWING FIGURES

Figure 2:
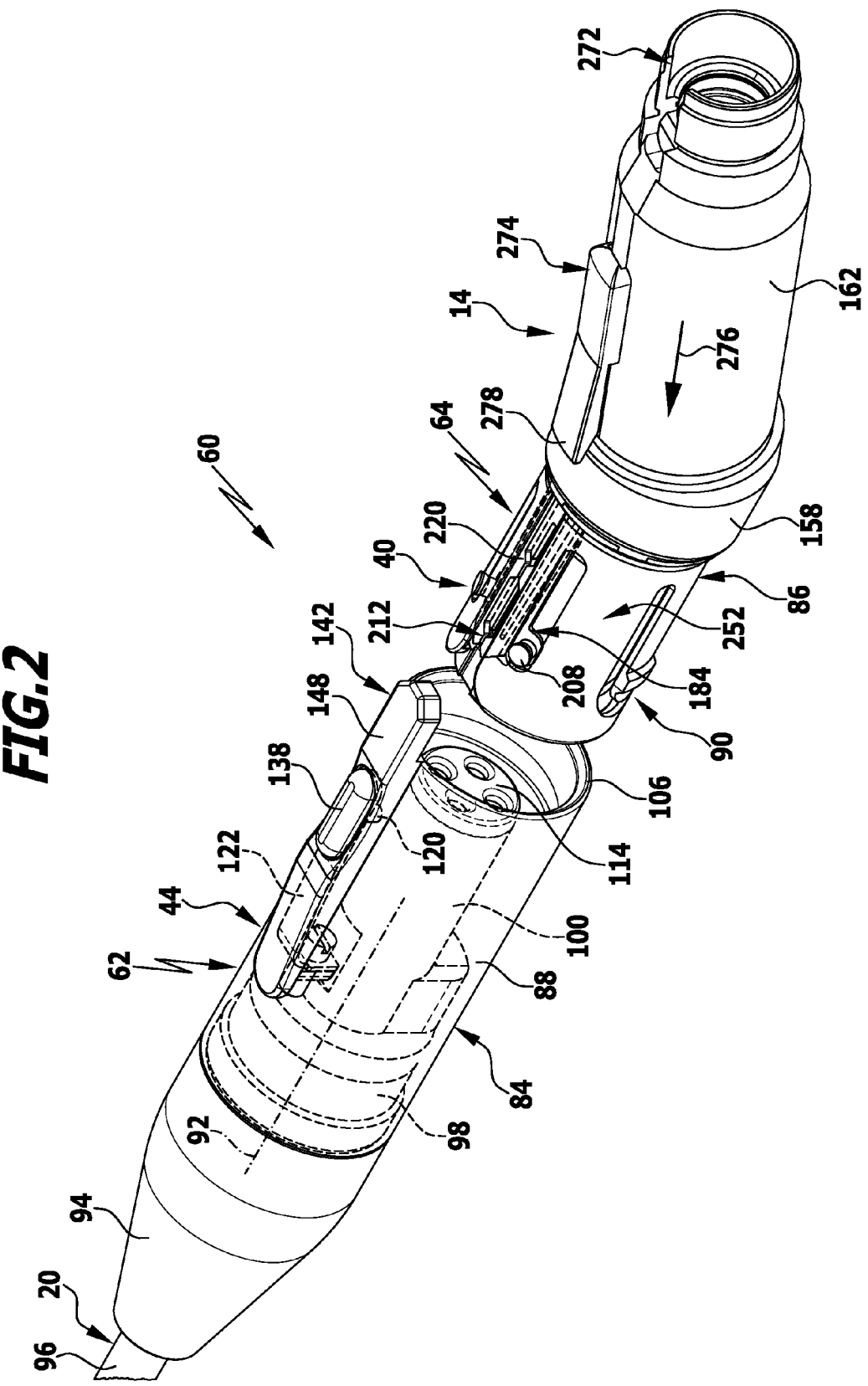
Figure 3:
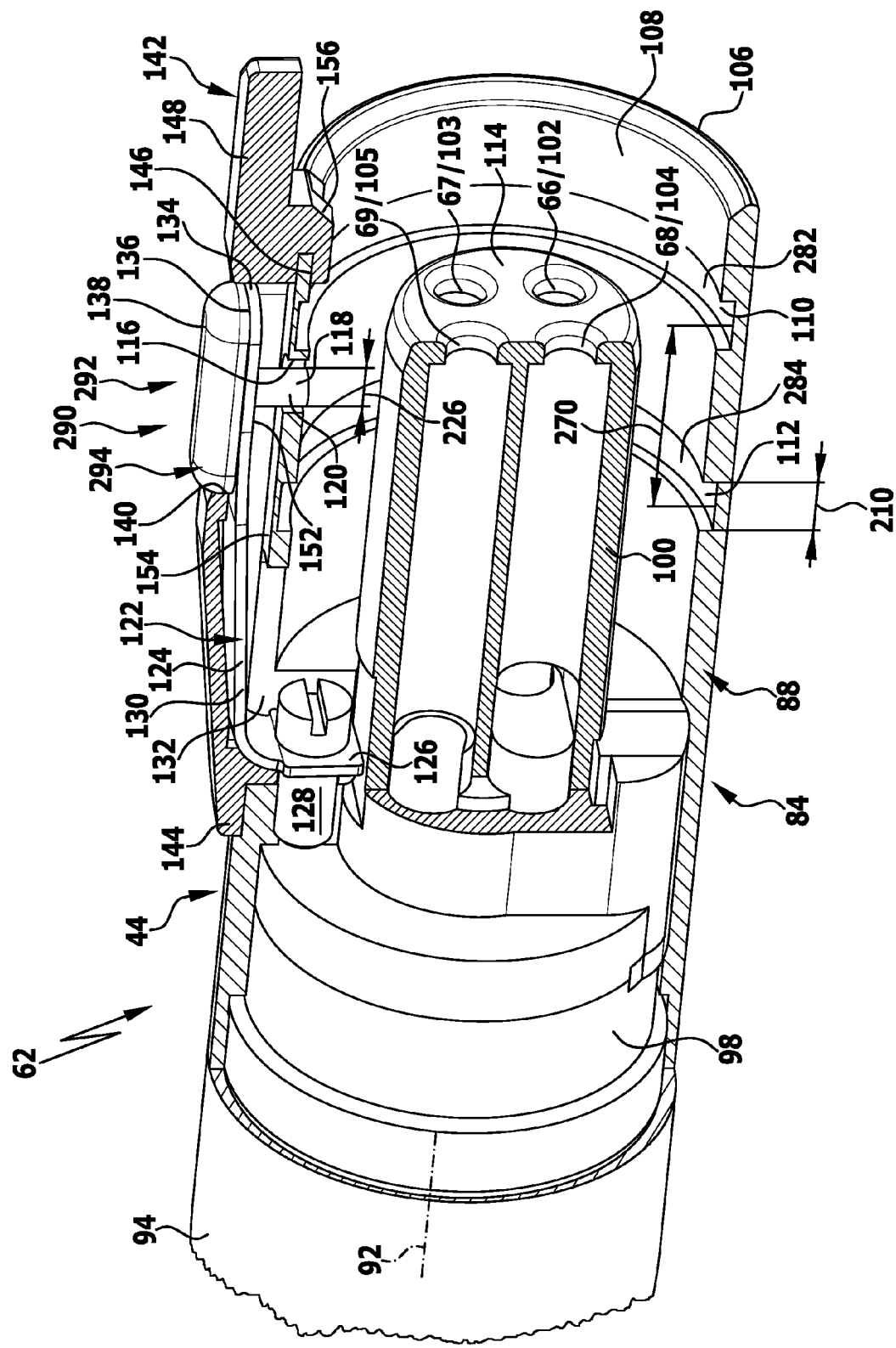
Figure 4:
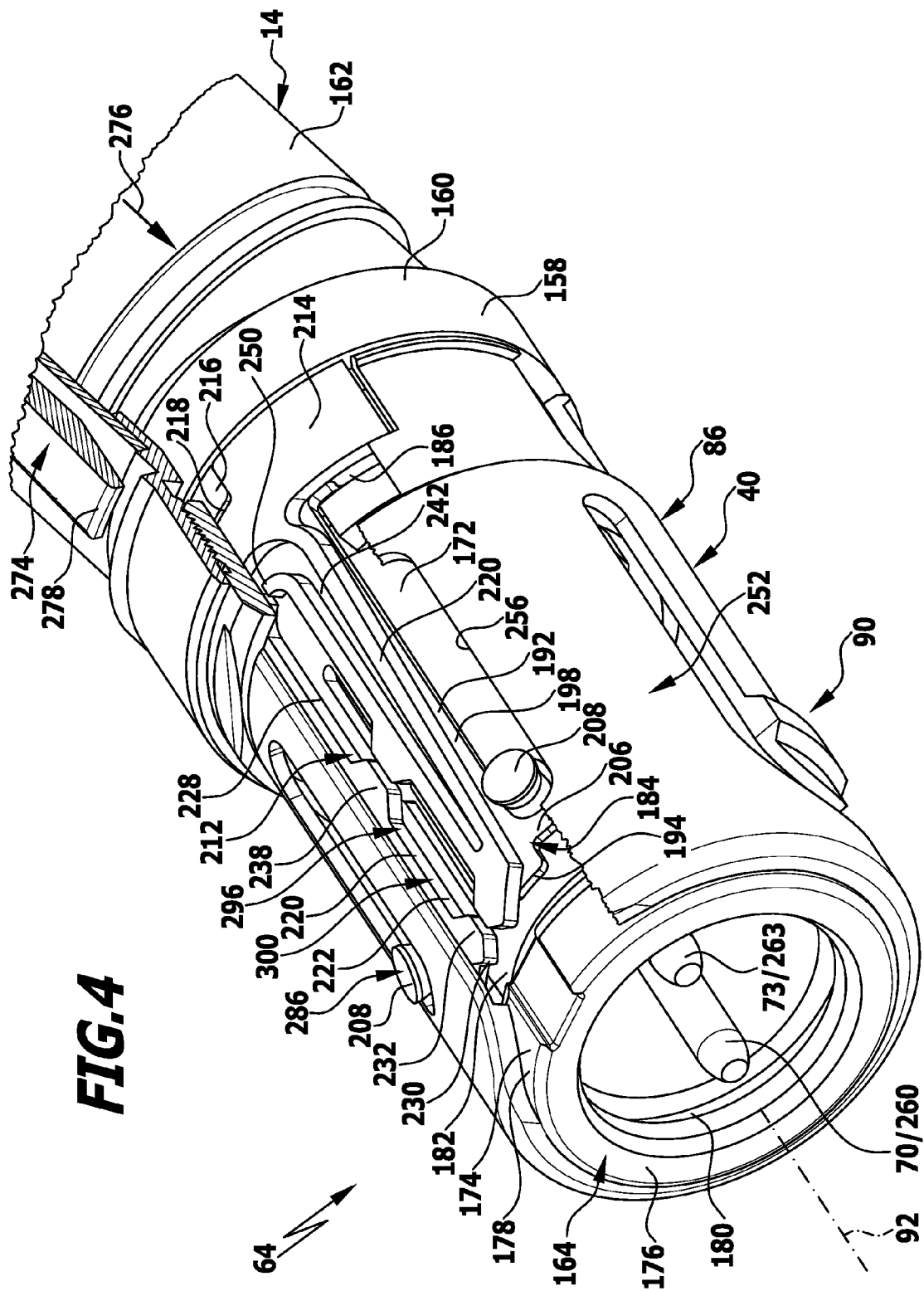
Figure 5:
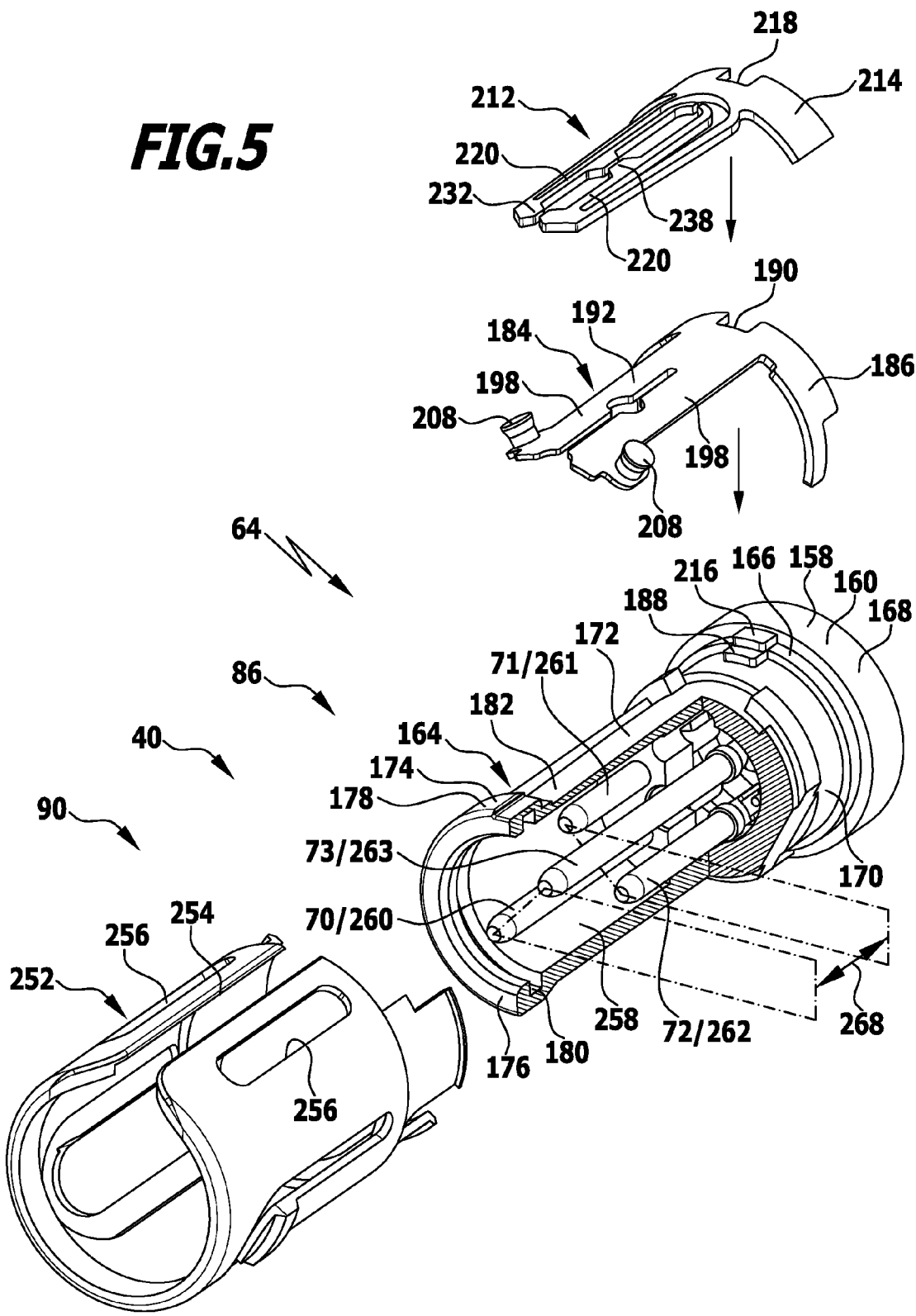
Figure 5A:
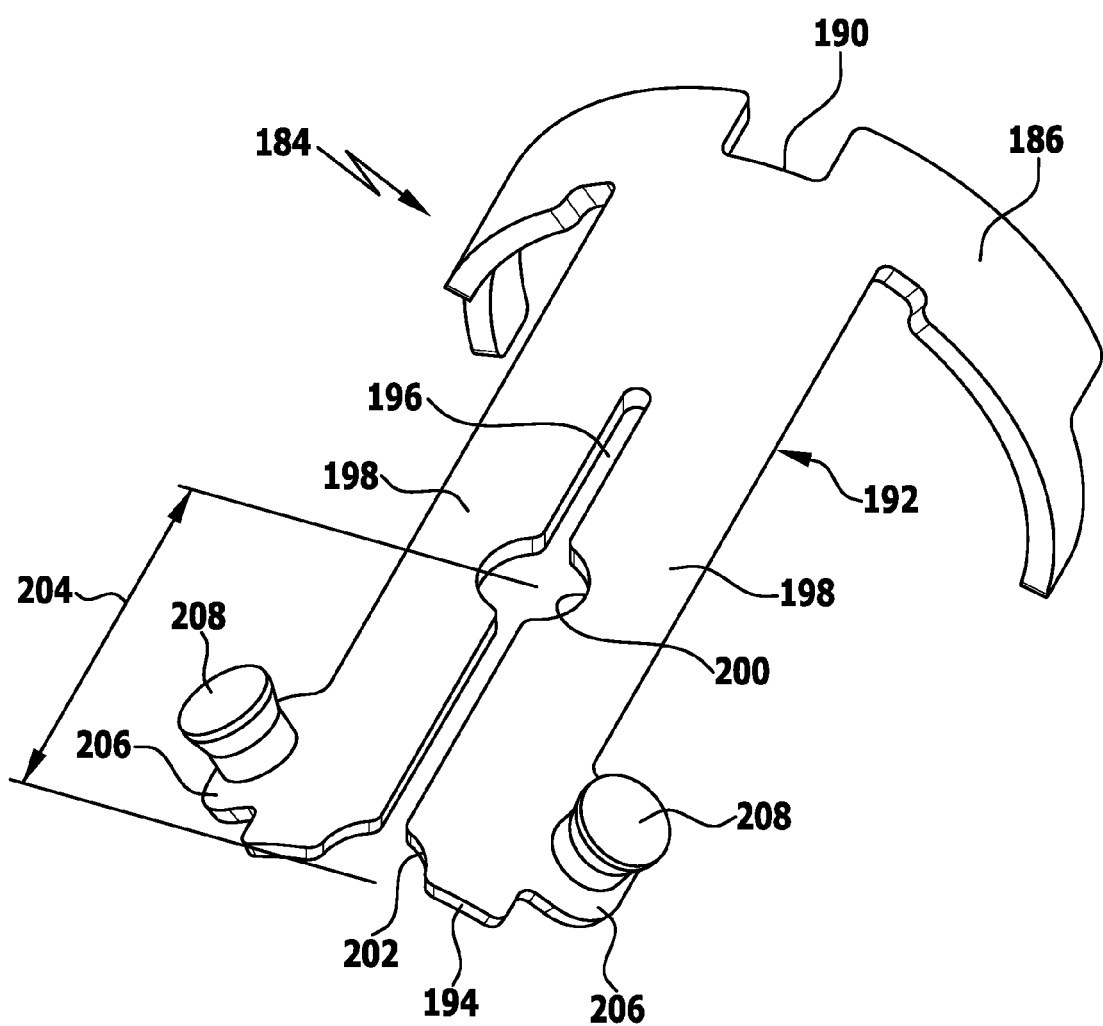
Figure 5B:
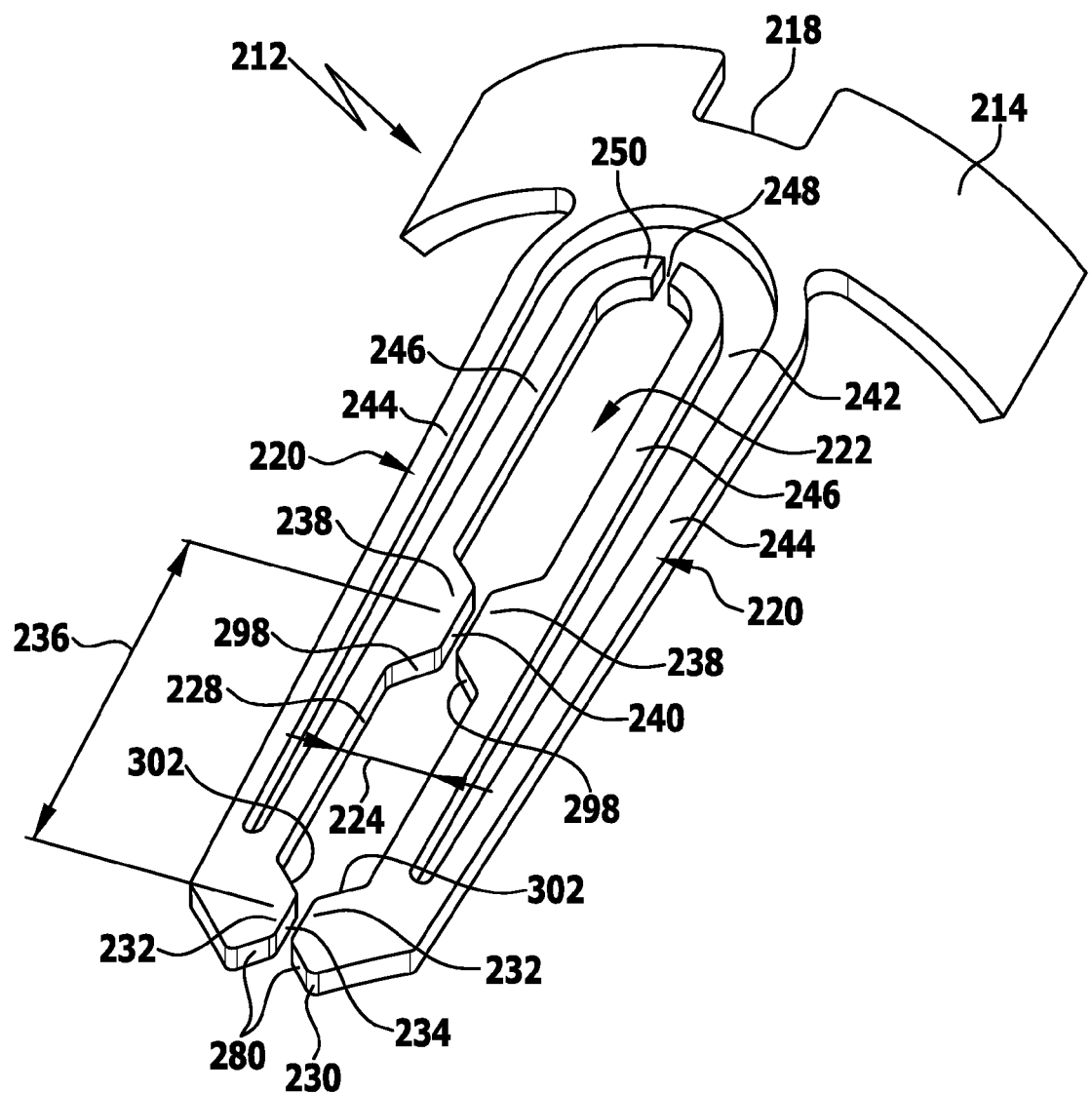
Figure 6:
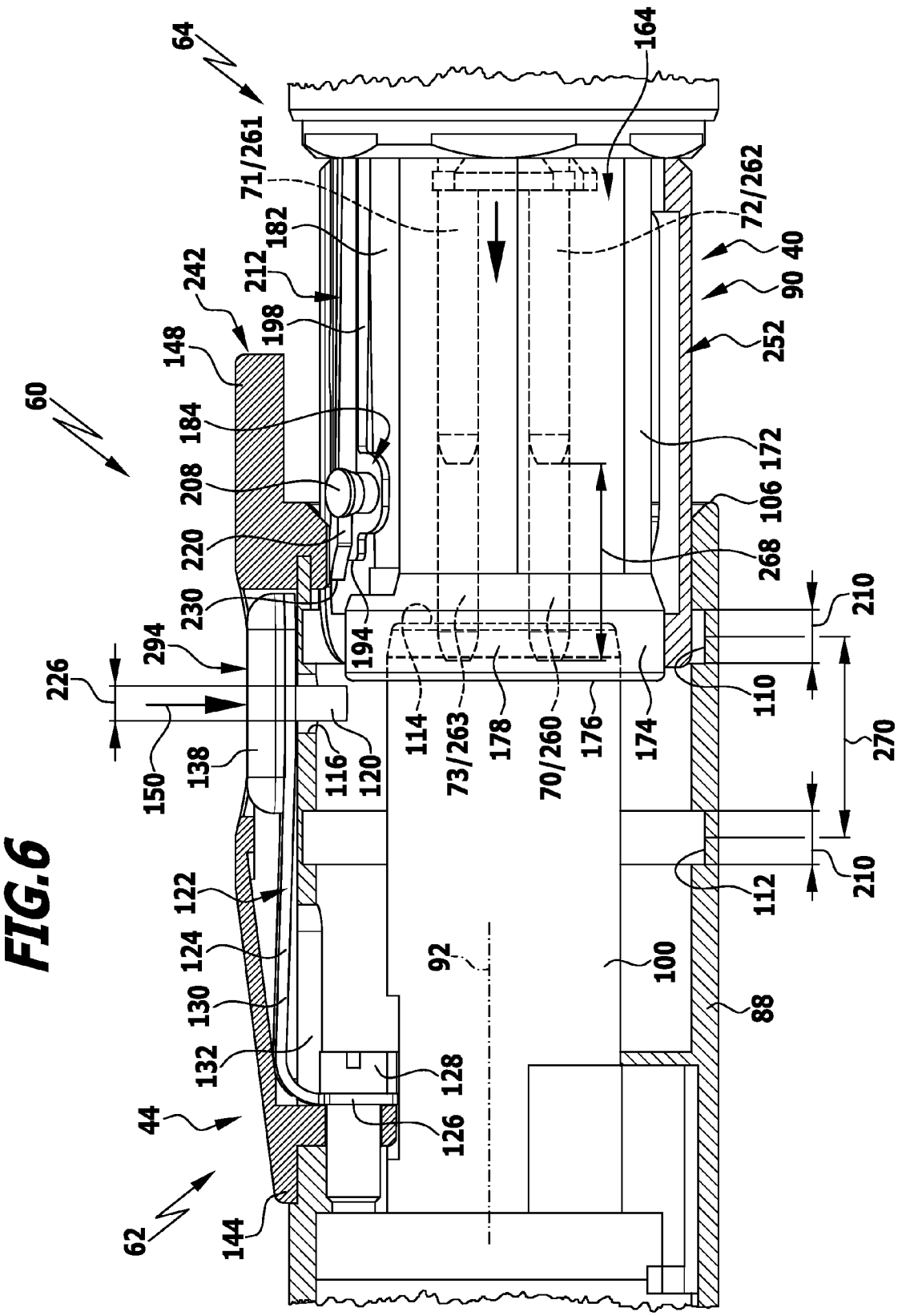
Figure 7A:
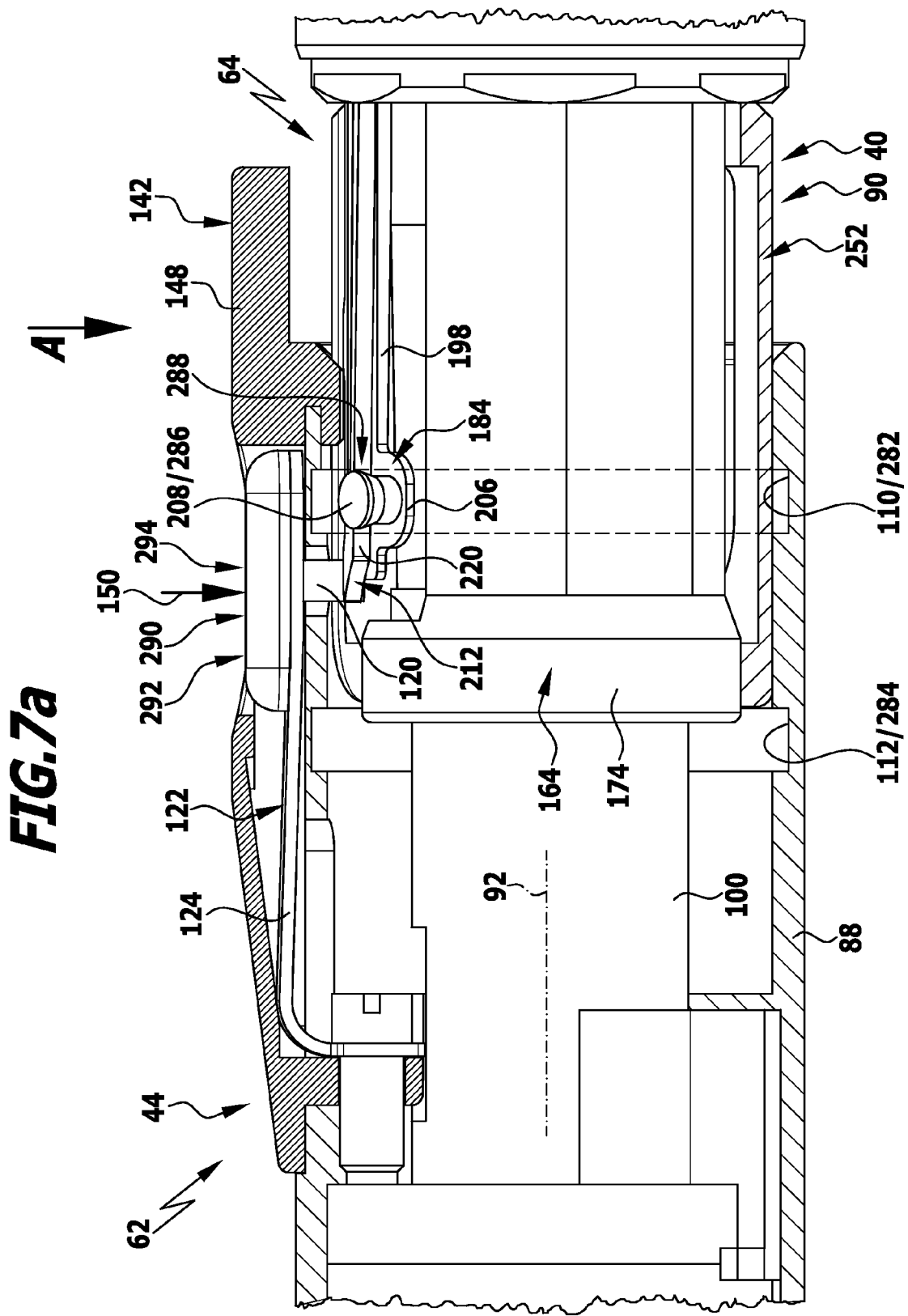
Figure 7B:
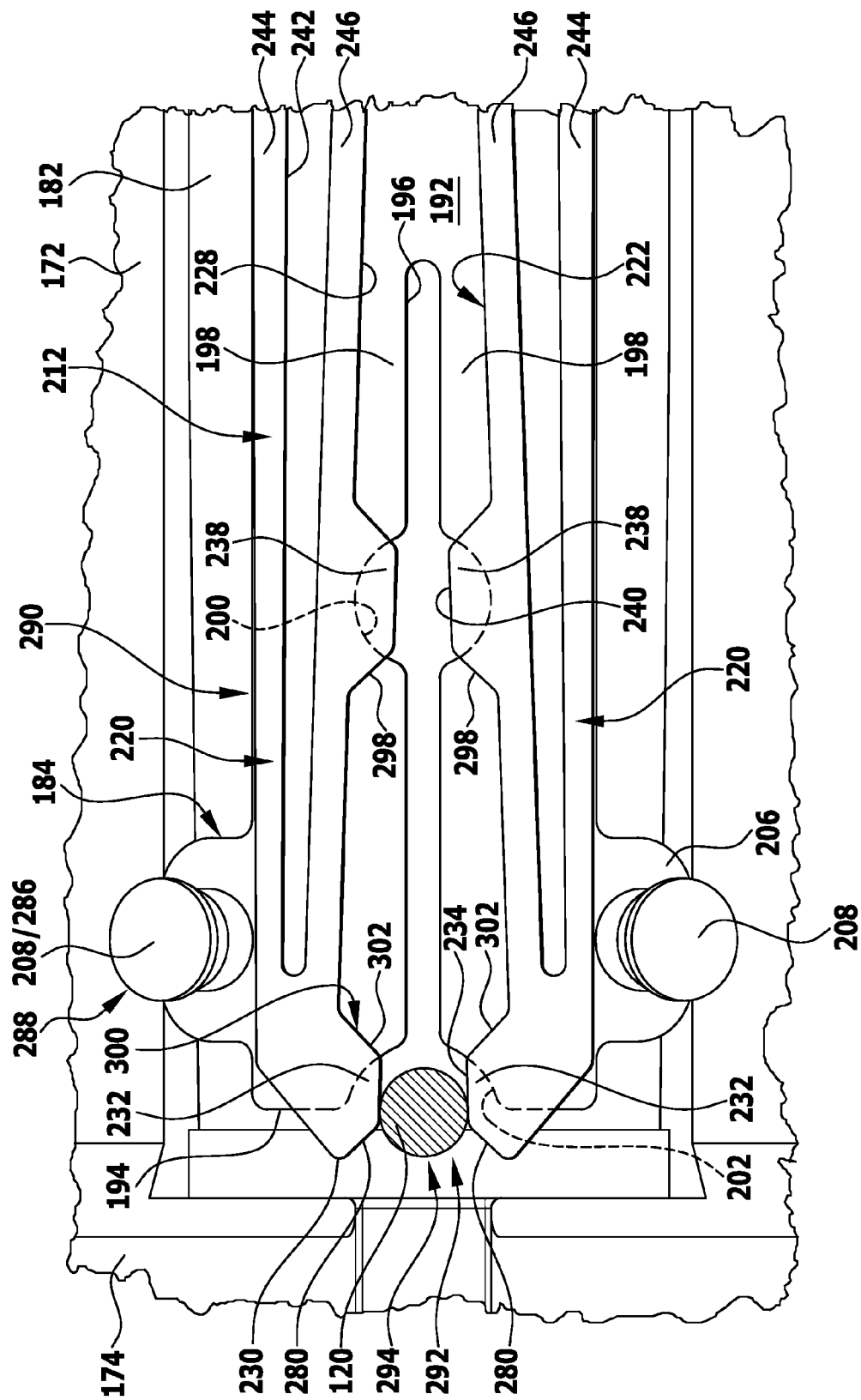
Figure 9:
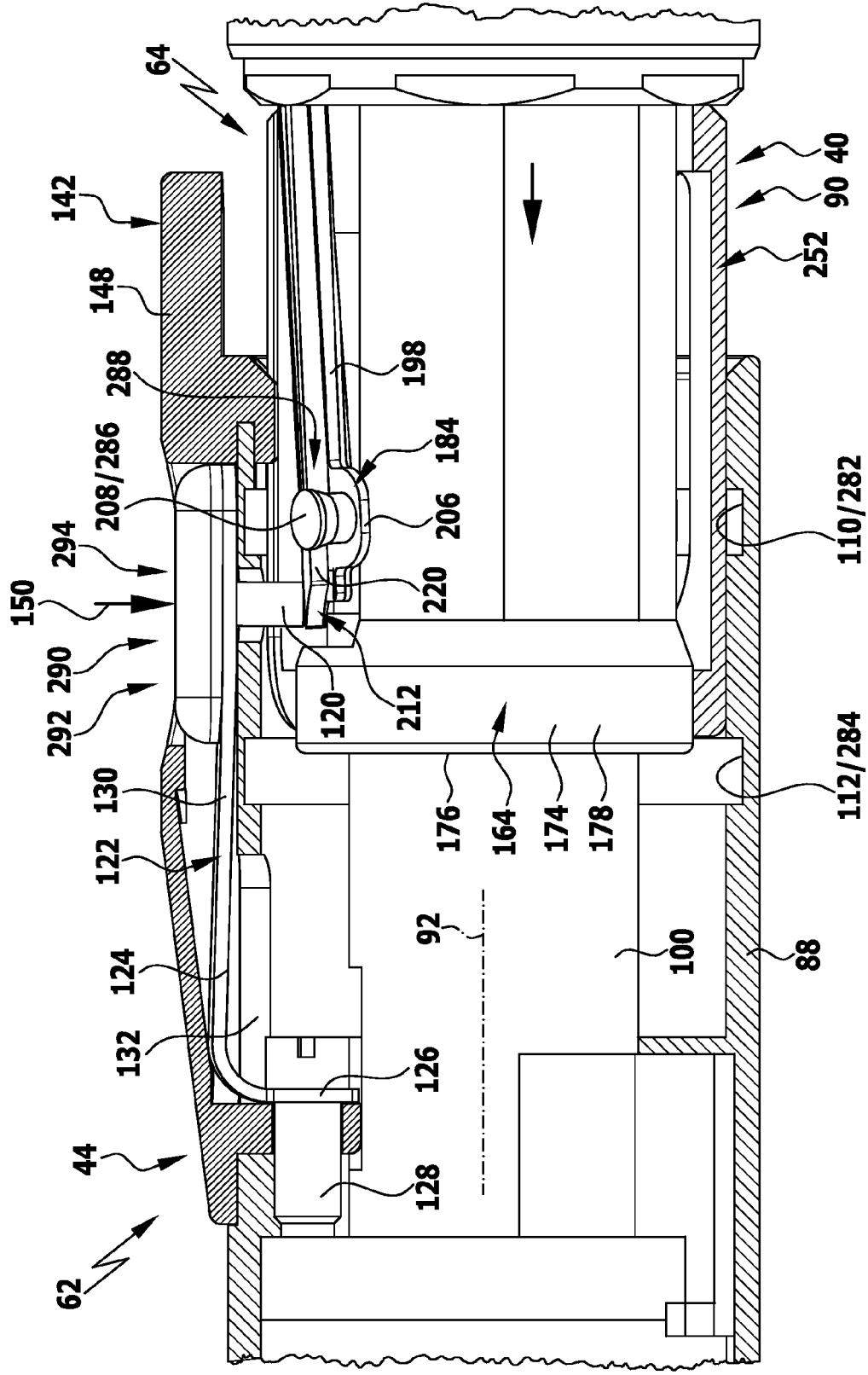
Figure 11B:
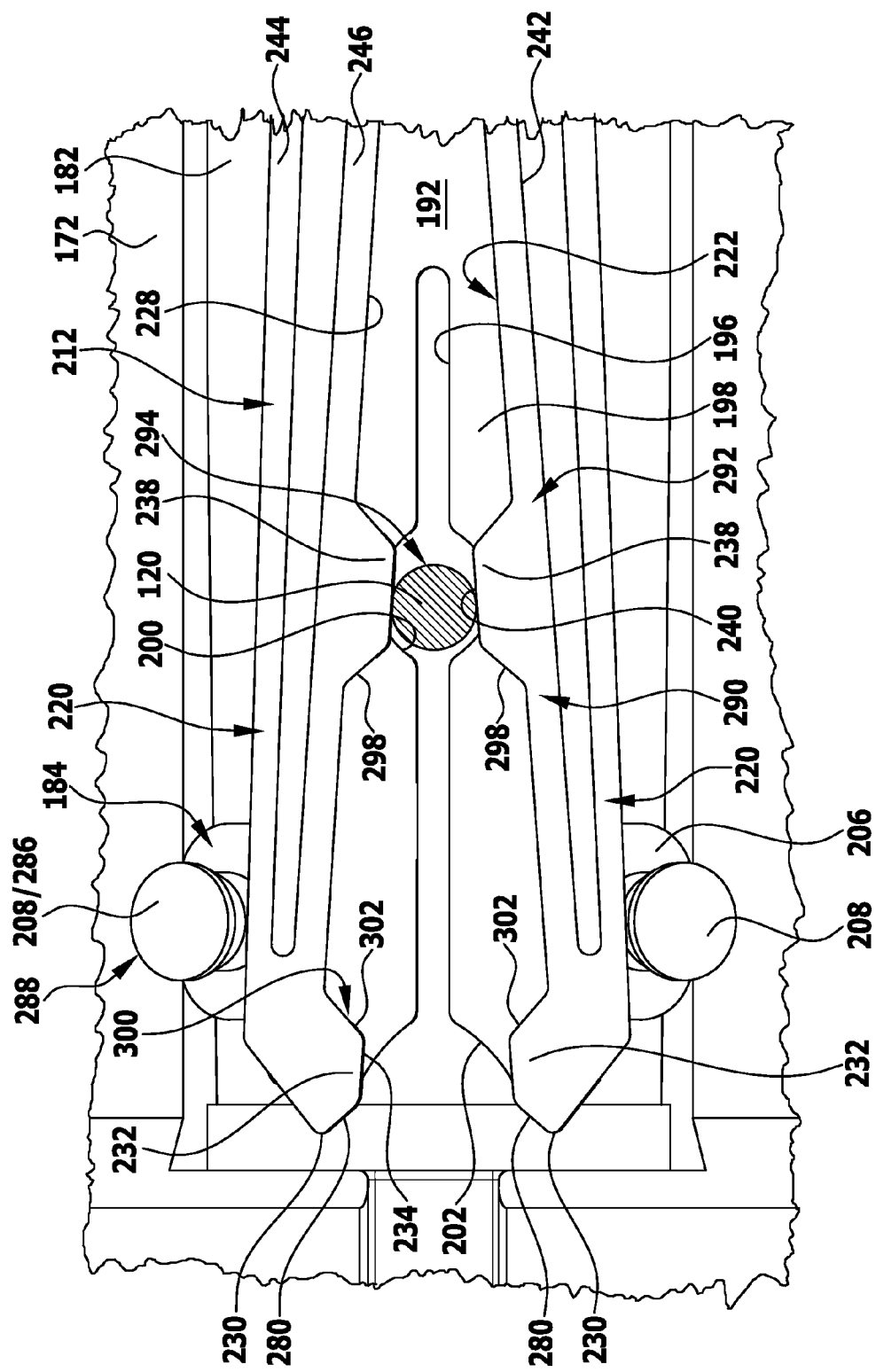
Figure 12A:
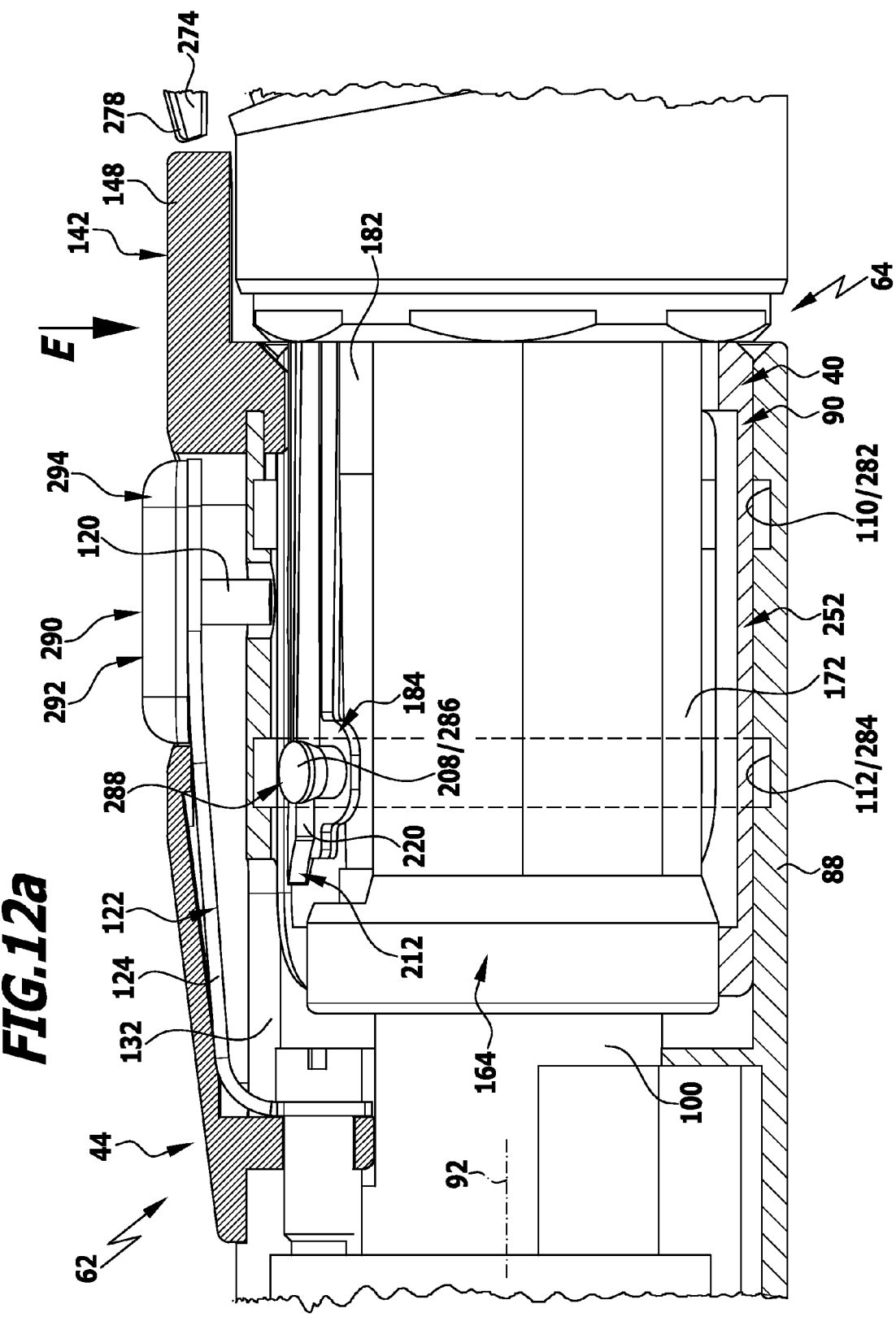
Figure 12B:
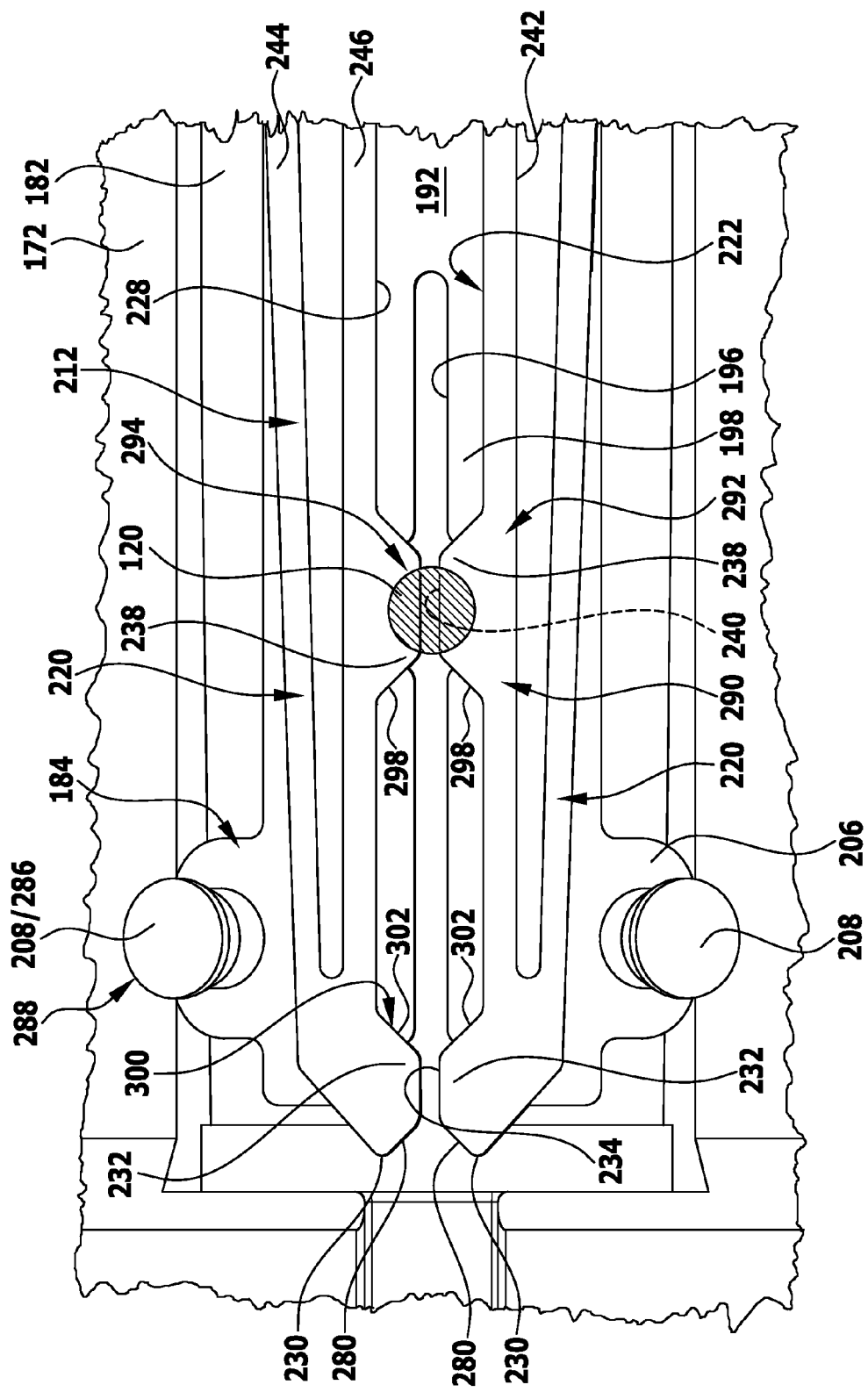
Figure 13:
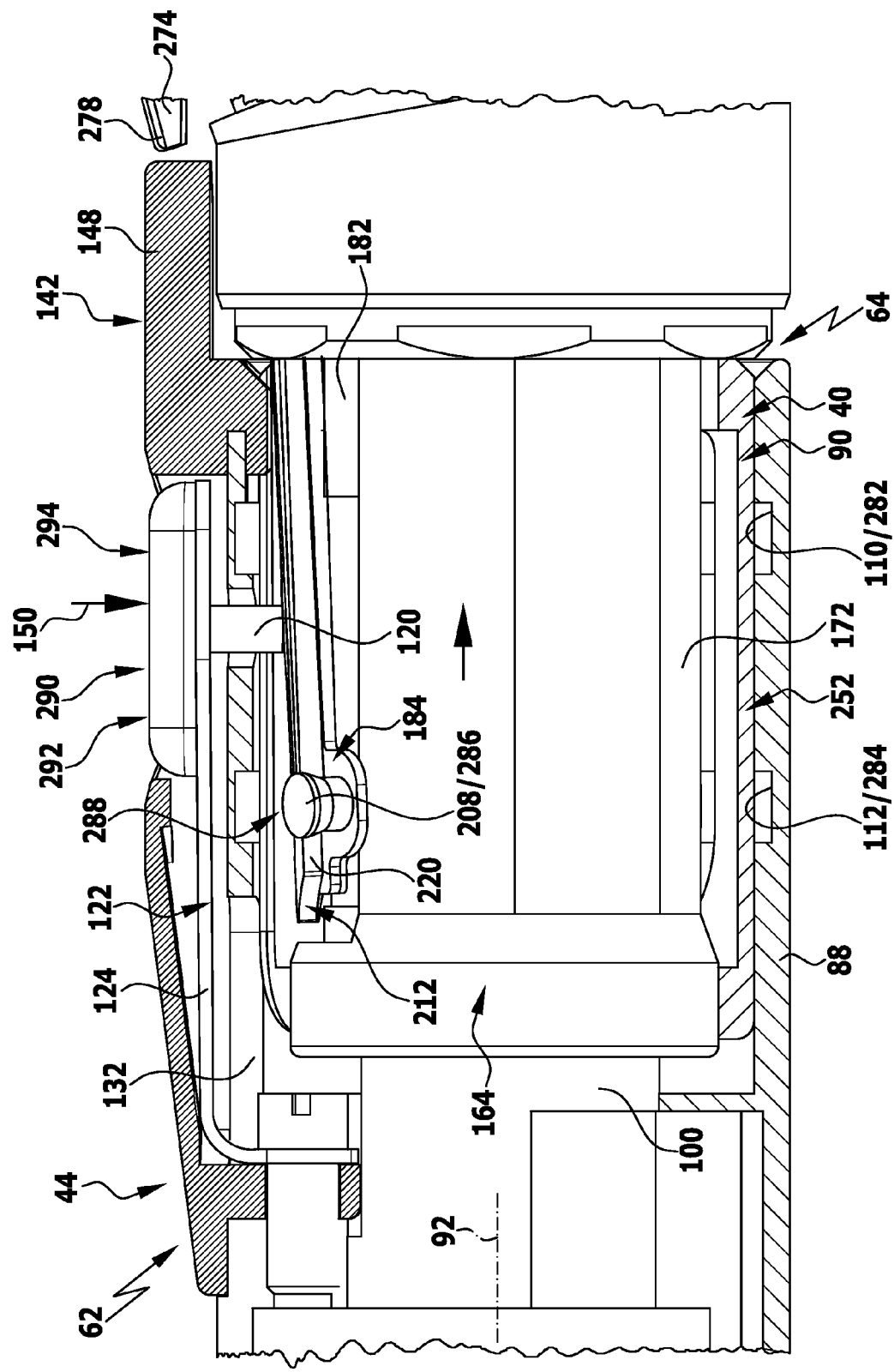

The foregoing summary and the following description may be better understood in conjunction with the drawing figures, of which:

FIG. 1: shows a schematic overall illustration of a surgical drive system;

FIG. 2: a schematic, perspective and partially cut-away illustration of a surgical coupling system;

FIG. 3: a partially sectional perspective illustration of a first coupling device of the coupling system with an unactuated releasing device;

FIG. 3a: a sectional view of the arrangement depicted in FIG. 3 with an actuated releasing device;

FIG. 4: a perspective, partially sectional view of a second coupling device of the coupling system;

FIG. 5: a partially sectional exploded illustration of the second coupling device;

FIG. 5a: a perspective view of the locking body of the second coupling device;

FIG. 5b: a perspective view of the control element of the second coupling device;

FIG. 6: a partially cut-away longitudinal view of the coupling system before the movement of the electrical coupling contacts of the two coupling devices into engagement;

FIG. 7a: a view of the coupling system analogous to FIG. 6 in the OFF position;

FIG. 7b: a partially sectional view in the direction of the arrow A in FIG. 7a;

FIG. 8a: a view of the coupling system analogous to FIG. 7a with an unactuated release member;

FIG. 8b: a view similar to FIG. 7b of the arrangement of the coupling system depicted in FIG. 7a in the direction of the arrow B;

FIG. 9: a view of the coupling system analogous to FIG. 8a with an actuated release member in the driving position of the control element;

FIG. 10a: a view of the coupling system analogous to FIG. 9 in the switching position during the transition from the OFF position into the ON position;

FIG. 10b: a view analogous to FIG. 8b of the arrangement of the coupling system depicted in FIG. 10a in the direction of the arrow C;

FIG. 11a: a view of the coupling system analogous to FIG. 10a in the ON position;

FIG. 11b: a view analogous to FIG. 10b of the arrangement of the coupling system in FIG. 11a in the direction of the arrow D;

FIG. 12a: a view of the coupling system analogous to FIG. 11a with an unactuated release member in the coupling position;

FIG. 12b: a view analogous to FIG. 11b of the arrangement of the coupling system depicted in FIG. 12a in the direction of the arrow E;

FIG. 13: a view of the coupling system analogous to FIG. 12a with an actuated release member and the control element in the driving position;

FIG. 14: a sectional perspective illustration of a second exemplary embodiment of a surgical coupling system in the separated position;

FIG. 15: a sectional longitudinal view of the coupling system depicted in FIG. 14 in the OFF position;

FIG. 16a: a schematic wiring diagram of the coupling system in the separated position;

FIG. 16b: a schematic wiring diagram of the coupling system in the OFF position; and FIG. 16c: a schematic wiring diagram of the coupling system in the ON position.

DETAILED DESCRIPTION OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a surgical coupling system comprising a first surgical coupling device and a second surgical coupling device each having at least two electrical coupling contacts that are moveable mechanically into engagement with one another, wherein the first and the second coupling device are completely separated from each other in a separated position and are mechanically in engagement with one another in a mechanical coupling position, characterized by an electrical switching device which, in the coupling position, is moveable from an OFF position, in which at least one first electrical coupling contact of the first coupling device and at least one first electrical coupling contact of the second coupling device are out of engagement, into an ON position in which the at least one first electrical coupling contact of the first coupling device and the at least one first electrical coupling contact of the second coupling device are in electrically conductive contact or engagement, and/or vice versa.

With the aid of the surgical coupling system that has been further developed in the proposed manner, it is then possible, in particular, to use the cooperating coupling devices as a switching device. In other words, a plug connection between the supply line and the hand-piece can therefore also be used simultaneously as a switch for example, this thereby enabling an operator to e.g. activate and then deactivate the electric motor of the hand-piece as required. The coupling system as a whole can thus exercise a dual function. On the one hand, it can make a mechanical connection between the hand-piece and a supply line for example. On the other hand, it can also be used as a switching device in order to enable the e.g. motor windings of an electric motor of the hand-piece to be energised as required. Due to this arrangement, it is possible, in particular, to equip the supply line with only so many connecting lines as the electric motor comprises motor windings. Consequently, the number of necessary electrical contact elements can be minimized and in particular, to the number of motor windings of the electric motor. In the case of conventional drive systems for example, one can thereby dispense with further lines for actuating the electric motor and, where necessary, for interrogating its type or design.

It is expedient if the first and the second coupling device each comprise at least one second electrical coupling contact and if the second coupling contacts are in electrically conductive contact or engagement with one another in the OFF position and in the ON position. In other words, it is thereby possible for example, to carry out an interrogation process in regard to the specific electrical characteristics of the hand-piece over the second electrical coupling contacts which are already in electrically conductive contact or engagement in the OFF position before the activation process, i.e. in particular, before energising the electric motor. For example, in the OFF position, a resistance test can be made by means of which the type of hand-piece can be unambiguously identified with certainty. Preferably for this purpose, there are provided in each case two second electrical coupling contacts, wherein the two second electrical coupling contacts of the hand-piece are connected together in electrically conductive manner via at least one motor winding.

It is particularly advantageous if the one of the two coupling devices comprises at least one first coupling element, if the other one of the two coupling devices comprises at least one second coupling element which is formed in correspondence with the at least one first coupling element, and if the at least one first and the at least one second coupling element are in engagement with one another in the coupling position. Due to the at least one first and at least one second coupling elements, a mechanical connection of the two coupling devices can, for example, be realized in a simple manner, namely in particular, independently of a switching status of the switching device. In other words, the coupling devices can adopt the coupling position and in that they can selectively adopt the ON position or the OFF position. The two coupling devices can thus mechanically form a unit, namely both in the ON position and in the OFF position.

The construction of the coupling system is particularly simple if the first coupling element is in the form of a coupling sleeve and if the second coupling element is in the form of a coupling plug that is insertable into the coupling sleeve. The coupling sleeve may be provided on either the first coupling device or the second coupling device. It is also conceivable to provide the coupling plug itself with a recess in which a further, second coupling plug that is arranged within the coupling sleeve can then engage. A stable mechanical connection between the two coupling devices can be established in this way.

In accordance with a further preferred embodiment of the invention, provision may be made for the coupling system to comprise a switching position securing device for mechanically securing the switching device in the ON position and in the OFF position. When the two coupling devices are coupled to one another, it can then be ensured by means of the switching position securing device in particular that the switching device cannot be transferred directly from the ON position into the OFF position and vice versa. For example, the switching device can be locked mechanically both in the ON position and in the OFF position. In this way and by appropriate design for example, the two coupling devices can be prevented from directly adopting the ON position during the coupling process, whereby the motor could be energised in an uncontrolled manner. In other words, preferably in the coupling position, the coupling devices can only initially adopt the OFF position by means of the switching position securing device. The switching device must then be deliberately transferred from the OFF position into the ON position by an operator.

It is expedient if the switching position securing device comprises a locking device for mechanically locking the first and second coupling devices adopting the coupling position in the ON position and in the OFF position and a releasing device for mechanically releasing the locking device. In particular, the locking device can be formed for automatically mechanically locking the two coupling devices in both the ON position and in the OFF position. For example, if the two mutually separated coupling devices are brought into engagement with one another, then this enables the locking device in particular to mechanically lock the two coupling devices initially in the OFF position. Then for example, the locking device can be released mechanically by the releasing device by means of an appropriate actuation of the releasing device in order to transfer the switching device from the OFF position into the ON position. The locking device preferably also automatically locks the coupling devices mechanically together in the ON position so that return of the switching device from the ON position into the OFF position is only possible by a deliberate actuation of the releasing device which then mechanically releases the locking device in order to transfer the coupling devices relative to each other back into the OFF position. In order to again separate the coupling devices from each other should this be necessary, then starting from the OFF position, the releasing device must be actuated again in order to release the locking device. A high degree of working reliability and deliberate switching i.e. transferral of the switching device from the ON position into the OFF position and vice versa, can thus be achieved.

It is advantageous if the locking device comprises first and second locking elements and also a third locking element, if the first and second locking elements are arranged or formed on the one of the two coupling devices, if the third locking element is arranged or formed on the other one of the two coupling devices and if the first and the third locking element are in engagement in the ON position and if the second and the third locking element are in engagement in the OFF position. Providing a locking device with at least the three aforesaid locking elements enables the coupling devices to be locked in at least two different positions relative to each other in a simple manner i.e. in the ON position and in the OFF position for example.

The locking device can be produced in a particularly simple manner if the first and the second locking element are in the form of first and second locking recesses and if the third locking element is in the form of a locking projection that is moveable into engagement with the first and with the second locking recess. For example, the locking projection can engage selectively in the first or in the second locking recess in order to thereby lock or secure the coupling devices relative to each other, for example, in the ON position and in the OFF position. Self-evidently, it would also be conceivable for the first and second locking elements to be in the form of locking projections and to provide at least one third locking element in the form of a locking recess.

In order to further simplify the construction of the coupling system, it is expedient if the first and the second locking recess are in the form of annular grooves that are mutually spaced in the axial direction and if the locking projection is in the form of a stud which is mounted such as to be moveable in the radial direction. For example, the annular grooves may be formed on the coupling sleeve or the coupling plug and the stud that is mounted such as to be moveable in the direction of the longitudinal axis or away from the longitudinal axis may be mounted or held on one of the two coupling devices in order to engage selectively in the annular grooves or to release them.

The coupling system can be constructed in a particularly compact manner, if the locking recesses are open in the direction of a longitudinal axis of the coupling sleeve. For example, the locking projection can thereby be in the form of a coupling stud which is mounted such as to be moveable in the radial direction in order to engage in one of the respective two locking recesses in the ON position and in the OFF position.

It is advantageous if the locking device comprises a biasing device for holding the locking elements in the ON position or in the OFF position. Due to the biasing device, it can thereby be ensured, in particular, that the locking elements engaging with one another in the ON position or in the OFF position can only be moved out of engagement against the action of the biasing device. Furthermore, during the process of moving the coupling devices into engagement, the biasing device may also optionally enable the locking elements to be moved automatically into engagement with one another as soon as the coupling devices are positioned relative to each other in such a manner that they can adopt the ON position or the OFF position.

It is expedient if the locking elements are moveable out of engagement only against a biasing force exerted by the biasing device. Consequently, the two coupling devices that are coupled to one another can only be deliberately transferred from the ON position or the OFF position into another position by the actuation of the releasing device and against the effect of the biasing device.

Preferably, the first and the third locking element and the second and the third locking element are arranged or formed such as to be moveable relative to each other in the radial direction with respect to a longitudinal axis of the coupling system for the purposes of being moved into and out of engagement. If the two coupling devices can be moved towards each other and brought into engagement with one another in the direction of the longitudinal axis of the coupling system for example, then a locking process or a process of releasing them from each other can only occur as a consequence of an actuation process in a direction transverse to the longitudinal axis, in particular in the radial direction. In this way in particular the working reliability of the coupling system can be increased.

It is advantageous if the releasing device is configured to move the first and third locking elements out of engagement from the ON position into a switching position in which the coupling devices are moveable relative to each other in the axial direction. This arrangement makes it possible for the coupling device that is prevented from relative movement in the ON position to be transferred by actuation of the releasing device into the switching position wherein they are moveable relative to each other in the axial direction, for example, in the direction of a longitudinal axis defined by the coupling system.

Furthermore it can be advantageous, if the releasing device is configured to move the second and third locking elements out of engagement from the OFF position into the switching position. In particular, the two coupling devices can be transferred from the OFF position into the switching position, preferably by a movement relative to each other in the axial direction, by actuation of the releasing device. Commencing from the OFF position for example, this makes it possible to separate the coupling devices from each other or to move into the ON position.

In particular, the usability of the coupling system for an operator can be further improved in that the releasing device comprises a movably mounted release member which is moveable from an unactuated position into an actuated position and/or vice versa. In particular, the release member can serve for moving the locking elements which are in engagement with one another in the ON or OFF position out of engagement.

It is expedient if the release member is moveable directly or indirectly into engagement or contact with the third locking element to transfer the locking device from the ON position or from the OFF position into the switching position. Thus, for example, by simple actuation of the release member and transferral thereof from the unactuated position into the actuated position in cooperation with the third locking element, the locking device can be transferred from the ON position or from the OFF position into the switching position in which, in particular, switch-over of the switching device from the OFF position into the ON position or vice versa is possible The surgical coupling system can be constructed in a particularly compact manner if the third locking element is arranged or mounted on a holding member and if the release member is moveable directly or indirectly into engagement or contact with the holding member to transfer the locking device from the ON position or from the OFF position into the switching position. Thus, due to the simple cooperation of the release member with the holding member, the third locking element for example can be moved in order to bring it out of engagement with the first or second locking element.

In particular, the construction of the surgical coupling system can be further simplified in a simple manner in that the biasing device comprises the holding member. For example, the holding member can be in the form of a spring element, preferably a leaf spring element which, following its deflection from a basic position, automatically goes back to the basic position without the intervention of further external forces. For example, the basic position of such a holding member can be that position in which the third locking element is in engagement with one of the other two locking elements.

In accordance with a further preferred embodiment of the invention, provision may be made for the releasing device to comprise at least one mechanical control element which is moveable from a driving position, in which the release member is moveable directly or indirectly into contact or engagement with the third locking element by means of the control element for transferring the locking device from the ON position or from the OFF position into the switching position, into a release position in which the release member is moveable neither directly nor indirectly into contact or engagement with the third locking element to an extent sufficient for transferring the locking device from the ON position or from the OFF position into the switching position. In this way, the control element makes it possible to create a simple mechanical control process for transferring, or even for not transferring, the locking device from the ON or OFF position into the switching position by means of the release member. Due to the special design of the control element, co-operation between the release member and the third locking element is not possible in the release position for transferring the locking device from the ON or OFF position into the switching position. Thus, for example, the control element can be used in order to prevent a direct transfer from the OFF position during the process of moving the coupling devices into engagement. In other words, a movement of the coupling devices towards one other as far as into the ON position for example can thus be prevented when the release member is actuated. Likewise for example in the reverse direction, an unintentional separation of the coupling devices from each other can be prevented when switching over from the ON position into the OFF position.

The coupling system can be constructed in a particularly compact manner if the control element is moveable in the direction of a longitudinal axis of the coupling system on which the coupling device comprising the third locking element is arranged or formed. The control element can thus be arranged or formed spatially very close to the third locking element, this thereby simplifying the co-operation of the control element and the third locking element.

It is expedient if the releasing device is constructed in such a manner that, in the actuated position of the control element, the release member transfers from the driving position into the release position for preventing the release member being moveable directly or indirectly into contact or engagement with the third locking element for transferring the locking device from the ON position or from the OFF position into the switching position. Particularly in the case where the release member adopts the actuated position, this arrangement can then prevent it from being brought into contact or into engagement with the third locking element in order to transfer the locking device into the switching position. In particular hereby as has already been explained, an unintentional transfer of both the ON position and the OFF position can thus be prevented. For example, if the two coupling devices are brought into engagement with one another and they adopt the switching position, then the coupling system can no longer be transferred into the ON position by a continuously actuated release member. In order to achieve this effect, the release member must firstly be transferred into the unactuated position whereby the control element can change back from the release position into the driving position so that a renewed actuation of the release member results in the third locking element being moved out of engagement with one of the two other locking elements. It is thus necessary for an operator to at least briefly release the release member, which can be spring-biased away from the longitudinal axis in the radial direction for example, in order to transfer the switching device into the respective other position after having reached the OFF position or the ON position or to separate the two coupling devices completely from one another.

It is advantageous if the releasing device is formed in such a manner that the control element is transferable from the release position into the driving position only by transferring the release member from the actuated position into the unactuated position. As has already been explained, it is due to this arrangement in particular that it can be ensured for preference that the coupling devices are initially locked automatically in the OFF position when they are moved into engagement. It is only when the release member is transferred from the actuated position into the unactuated position that the control element is quasi activated again in such a way that the third locking element can be moved back out of engagement with one of the two other locking elements as a result of a further actuation of the release member. For example, the coupling system can then be configured in such a way that in the case of an actuated release member the coupling devices can be brought into engagement with one another and the locking device then blocks or secures the coupling system automatically in the OFF position. In a next step, the control element can be transferred from the release position into the driving position after releasing the release member. After a repeated actuation of the release member, the coupling system can then be transferred from the OFF position into the ON position. Therefore, in the reverse order, the switching device can be transferred from the ON position into the OFF position and afterwards, if necessary, the switching device can again be transferred into the ON position or the coupling system into the separated position. In other words, when the release member is actuated, the coupling system can only be moved into the next position on each occasion, thus for example, from the separated position into the OFF position or from the OFF position into the ON position or from the ON position into the OFF position or from the OFF position into the separated position. Consequently, direct transfer of the coupling system from the separated position into the ON position via the OFF position for example or from the ON position into the separated position via the OFF position is not possible.

It is advantageous if the releasing device is formed in such a manner that the release member is moveable directly or indirectly into contact or engagement with the third locking element for transferring the locking device from the ON position or from the OFF position into the switching position only when in the driving position. The effect can thereby be achieved in particular, especially when in the release position, that the release member is not moveable into contact or engagement with the third locking element in such a manner that the locking device can be transferred from the ON position or from the OFF position into the switching position.

It is advantageous if the control element comprises at least one first control projection that is associated with the first locking element and at least one second control projection that is associated with the second locking element, both control projections being moveable transversely relative to a direction of movement of the release member for transferring the control element from the driving position into the release position and vice versa. For example, in the case where a direction of movement of the release member is oriented transversely relative to a longitudinal axis of the coupling system in order to transfer the locking device from the ON or OFF position into the switching position, a movement of the control projections can take place in a direction transverse to the direction of movement of the release member, thus in particular, in the peripheral direction taken with reference to the longitudinal axis of the coupling system or perpendicularly to the longitudinal axis. For example, in the actuated position thereof, the release member can come into contact with the control projections in such a manner that they can be transferred from the driving position into the release position transversely relative to the indicated direction of movement of the release member during the transition from the actuated position into the unactuated position. This makes it possible, particularly with the release member in the actuated position, to automatically transfer the control element from the driving position into the release position in the course of a movement of the coupling devices towards one another or away from each other in order to prevent the release member from being directly or indirectly moveable into contact or engagement with the third locking element in order to move the locking elements out of engagement from one another when they are in engagement with each other.

It is expedient if there are provided two first and/or two second control projections which are spaced from each other by a greater distance in the release position than in the driving position. The proper functioning of the coupling system can thereby be increased for example. In particular, the spacing between the control projections in the release position can be large enough that the release member can engage between them without hindrance and they cannot act as drivers upon actuation of the release member or the transferral thereof from the unactuated position into the actuated position in order to move the third locking element out of engagement with one of the other two locking elements.

It is advantageous if the first control projections and/or the second control projections are separated from each other by a slot in which the release member engages in the actuated position as a consequence of a movement of the two coupling devices towards one another or away from each other for forcibly moving the control projections away from each other in opposite directions into the release position. This, for example, can be effected in that the mutually associated control projections are pivoted or shifted away from each other by the introduction of the release member in the actuated position into the slot, whereby the spacing therebetween is increased. For example, the release member can be short enough that in the actuated position thereof it engages between the control projections that have been transferred into the release position and thus can come neither directly nor indirectly into contact with the third locking element in order to move the latter out of engagement with one of the two other locking elements.

Furthermore, it can be expedient if the releasing device comprises a restoring device for automatically transferring the control element from the release position into the driving position as soon as the release member is transferred from the actuated position into the unactuated position. In order to transfer the control element back into the driving position when its functionality is quasi switched off due to a continuously actuated release member, it is merely necessary to transfer the release member into the unactuated position. The restoring device then automatically transfers the control element from the release position, in which it cannot act as a driver for the release member, into the driving position.

In accordance with a further preferred embodiment of the invention, provision may be made for the first and the second coupling device to each comprise two first and two second electrical coupling contacts. For example, one or more characteristics of the hand-piece can be interrogated via the second electrical coupling contacts which are already in contact with one another in the OFF position by measuring the flow of current through the hand-piece upon the application of a test voltage in order to automatically determine the type of hand-piece by means of a control and/or regulating device and then to initiate powering of the electric motor of the hand-piece in accordance therewith.

It is advantageous if three of the four electrical coupling contacts are connected in electrically conductive manner to a respective motor winding of the electric motor. Consequently, three motor windings of the electric motor can be directly controlled via three coupling contacts for example. Likewise for example, the fourth electrical coupling contact can be indirectly connected in electrically conductive manner to a motor winding via a resistance connected in series therewith. Preferably, the fourth electrical coupling contact is one of the two second electrical coupling contacts.

Furthermore, it can be expedient if the coupling system comprises an electrical supply line having a first and a second end, if the first coupling device is arranged or formed at the first end and if the second end is connected or releasably connectable to a control and/or regulating device for the control and/or regulation of a surgical electric motor. Self-evidently, as an alternative, it would also be conceivable to provide the second coupling device at the first end of the supply line. For example, the first coupling device of the supply line can be coupled to or brought into engagement with a second coupling device, which for example, can be arranged on a surgical hand-piece which can be selectively equipped with or without an electric motor.

It is advantageous, if the coupling system comprises a surgical hand-piece having an electric motor for driving a surgical tool which is coupled to or couplable with the hand-piece, which hand-piece has a proximal and a distal end, at which proximal end the second coupling device is arranged or formed. Then for example, such a surgical hand-piece can be coupled to or brought into engagement with a supply line comprising a first coupling device. When the supply line and the hand-piece have been brought into engagement with one another by means of their two coupling devices, then, as described above, the coupling system comprising the two coupling devices can also be used selectively for switching purposes, i.e. for purposefully actuating the electric motor of the hand-piece. Further switching devices for switching the electric motor on or off are then no longer compellingly necessary.

In order to enable the type of hand-piece that is connected thereto to be automatically determined by a control and/or regulating device for example, it is expedient if the hand-piece comprises at least one coding element for coding the type of the hand-piece. For example, the coding element can be in the form of an electronic circuit. In particular thereby, it may be an RFID chip.

The type of hand-piece can be coded in a particularly simple manner, if the at least one coding element comprises a resistance which has a resistance value that is associated with or corresponds to the type of the hand-piece. As described above for example, in the OFF position, the resistance value which corresponds to a certain type of hand-piece can be determined by applying an electrical voltage to the second electrical coupling contacts and then measuring the current flow. With a knowledge of the resistance values to be expected for the available hand pieces, the type of the actually present hand-piece can then be determined in a simple manner.

Preferably, the at least one coding element is connected to a second coupling contact of the second coupling device in electrically conductive manner. In this way, it can be used in the OFF position for example in order to recognize the type of the hand-piece automatically.

In accordance with a further preferred embodiment of the invention, provision may be made for the hand-piece to comprise a tool coupling device for coupling the hand-piece to a working tool in releasable manner. For example, the tool coupling device can be arranged and formed in such a manner that the working tool is moveable into engagement with the hand-piece or with the distal end thereof. This has the advantage that different working tools can be selectively coupled to the same hand-piece in dependence on the surgical procedure that is to be effected.

Expediently, the tool coupling device is moveable from a tool coupling position, in which the hand-piece is coupled to a working tool, into a tool separating position in which the working tool is separable from the hand-piece. Such a tool coupling device enables a working tool to be easily released from the hand-piece in the tool separating position.

It is particularly advantageous if the tool coupling device is blocked in the ON position for preventing transfer from the tool coupling position into the tool separating position. In this way in particular, an operator can be prevented from inadvertently separating the working tool from the hand-piece if the coupling system adopts the ON position. In other words, separation of the working tool from the hand-piece whilst the electric motor is running can thereby be especially prevented.

It is expedient if the tool coupling device comprises at least one tool coupling member which is mounted or held movably on the hand-piece and is moveable only in the separated position or in the OFF position for directly or indirectly releasing the working tool in order to separate it from the hand-piece, and if the locking device in the ON position secures the at least one tool coupling member in the tool coupling position. For example, this can thereby prevent an operator from actuating or moving the tool coupling member when the coupling system is in the ON position. The tool coupling device is thus quasi secured or disabled in the ON position. Inadvertent release of the working tool from the hand-piece whilst the electric motor is in operation is then no longer possible.

It can be ensured in a particularly simple manner that the second electrical coupling contacts are in contact or engagement with one another both in the ON position and in the OFF position, if the first electrical coupling contacts or at least a part thereof are shorter than the second electrical coupling contacts. This, for example, enables the second electrical coupling contacts of the two coupling devices to come into contact with one another or engage each other during the actual process of moving the two coupling devices towards one another, whereas this only becomes possible for the first electrical coupling contacts after the two coupling devices have been moved still further towards one another. Consequently, the ON position and the OFF position can be defined in a simple manner by appropriate relative positioning of the two coupling devices.

The present invention further relates to a surgical drive system comprising at least one surgical hand-piece having a drive in the form of an electric motor and at least one electrical supply line, which supply line comprises a first end that is connectable to the at least one hand-piece in releasable manner and a second end that is connected or connectable in releasable manner to a control and/or regulating device for controlling and/or regulating the electric motor, characterised by a coupling system for the electrical and mechanical connection of the hand-piece and the supply line, said coupling system comprising a first surgical coupling device and a second surgical coupling device each having at least two electrical coupling contacts that are moveable mechanically into engagement with one another, wherein the first and the second coupling device are completely separated from each other in a separated position and are mechanically in engagement with one another in a mechanical coupling position, characterized by an electrical switching device which, in the coupling position, is moveable from an OFF position, in which at least one first electrical coupling contact of the first coupling device and at least one first electrical coupling contact of the second coupling device are out of engagement, into an ON position in which the at least one first electrical coupling contact of the first coupling device and the at least one first electrical coupling contact of the second coupling device are in electrically conductive contact or engagement, and/or vice versa.

A drive system that has been further developed in such a manner thus also enables switching of the hand-piece due solely to the special construction of the coupling system. A further switching device is then no longer absolutely necessary. Altogether then, the thus improved surgical drive system also has the advantages mentioned above in connection with preferred embodiments of the surgical coupling systems.

It is advantageous if the drive system comprises an appropriate control and/or regulating device for the purposes of controlling and/or regulating the electric motor. In particular, this can be formed for cooperating with the surgical hand-piece in such a way that the type of the hand-piece can be automatically interrogated and recognized when the coupling system adopts the OFF position.

A surgical drive system bearing the general reference symbol 10 is illustrated schematically in FIG. 1 wherein said system comprises a control and/or regulating device in the form of a controller 12, five hand pieces 14a to 14e, two shaver hand pieces 16a and 16b, a pistol hand piece 18, two supply lines in the form of terminal cables 20 and 22 and also a foot control 24. All of the hand pieces mentioned above comprise an integrated electric motor serving as a drive means and thus form drive units.

The controller 12 comprises a flat screen 28 in the form of a touch screen which is arranged in a housing 26. Three control elements 30a to 30c and 30d to 30f are arranged on each side of the screen 28.

Arranged in a line below the screen 28, are two switches 32a and 32b having a terminal socket 34 for the connection of the foot control 24 via an optional terminal cable 25 and also two terminal sockets 36a and 36b for the connection of the terminal cables 20 and 22 with which the hand pieces can be connected to the controller 12. Moreover, as an option, a connector 38 for a fluid system for the supply and removal of fluids from a region being operated on can be provided, and also for example, for the servicing of rinsing or extraction channels to not illustrated gear units or tools which are connectable to the hand pieces 14, the shaver hand pieces 16 or the pistol hand piece 18 and which together with the hand pieces form surgical instruments of the drive system 10.

The hand pieces 14a to 14e each comprise a cable coupling 40a to 40e which is arbitrarily connectable to a coupling piece 44 of the terminal cable 20 or to a coupling piece 46 of the terminal cable 22. In like manner, the two shaver hand pieces 16a and 16b and also the pistol hand piece 18 each have a respective cable coupling 40f, 40g and 40h which are connectable to one of the two coupling pieces 44 or 46.

At the respective other ends thereof, the hand pieces 14a to 14e are each equipped with gearing or tool couplings that define tool coupling devices 42a to 42e to which not illustrated gear units equipped e.g. with drills, saw blades or the like can be coupled, and which can be driven by the hand pieces 14a to 14e. Depending upon the arrangement, the hand pieces 14a to 14e can also be directly equipped with not illustrated working tools such as drills or saw blades for example, for the purposes of forming surgical instruments.

The hand pieces 14a to 14e are preferably sensor-less, i.e. they do not incorporate sensors for determining the rotational speed of the hand pieces 14a to 14e when in operation. As schematically illustrated in FIG. 1, the hand pieces of the drive system 10 differ not only outwardly, but also in regard to their internal construction. This means that the electric motors built-into the hand pieces 14a to 14e can be of different types and may, for example, differ in their characteristics such as minimum rotational speed, maximum rotational speed, maximum current rating and maximum torque for example. In addition, as in the case of the two shaver hand pieces 16a and 16b, gearing can be integrated therein, and this may optionally be integrated into gear units that are couplable to the hand pieces 14a to 14e and also to the pistol hand piece 18. The gear units themselves can also be additionally equipped with different instrument tips in the form of surgical tools in dependence upon the design.

Moreover, the shaver hand pieces 16a and 16b each comprise a shaver coupling 48a or 48b for the connection of a shaver attachment for usage in the field of arthroscopy for example.

The terminal cables 20 and 22 are provided with couplings 21 and 23 for the connection to the controller, these being connectable to the terminal sockets 36a and 36b.

The foot control 24 is connected to the controller 12 via a wireless data transmission arrangement such as an infrared or a radio transmission system for example. Optionally, it is also possible to connect the foot control 24 by means of a coupling piece 50 of the terminal cable 25 which is connectable to the terminal socket 34. Two foot-operable switches 54a and 54b are arranged on a housing 52 of the foot control 24 by means of which, in particular, left or right rotation of the hand pieces can be regulated.

The pistol hand piece 18 is equipped with two control devices 56, wherein the control device 56a may be provided for activating right-hand rotation of the motor and control device 56b for activating left-hand rotation of the motor for example.

The terminal cables 20 and 22 differ in that, in contrast to the terminal cable 20, the terminal cable 22 is provided with an actuating lever 58 by means of which an operator can activate the motor of a hand-piece 14, a shaver hand-piece 16 or the pistol hand piece 18. The function of the actuating lever 58 is that of a rotational speed controller by means of which the rotational speed of the motor can be set by an operator.

In addition to the actuating lever 58 provided for the terminal cable 22 which thus forms a rotational speed setting device on the terminal cable 22, there may also be provided a surgical coupling system which bears the general reference symbol 60 and is illustrated schematically in FIG. 2. Thus, both the coupling piece 44 on the terminal cable 20 and the coupling piece 46 on the terminal cable 22 can be in the form of a first coupling device 62, a cable coupling 40 on the hand-piece 14 which is illustrated schematically in FIG. 2 can be in the form of a second coupling device 64. The coupling system 60 is illustrated in FIG. 2 in a separated position in which the two coupling devices 60 and 62 are completely separated from each other, thus in particular, are mechanically out of engagement. Each of the two coupling devices 62 and 64 comprises four electrical coupling contacts. The first coupling device 62 comprises the coupling contacts 66, 67, 68 and 69, the second coupling device 64 comprises the coupling contacts 70, 71, 72 and 73. The terminal cable 20 comprises just three lines 74, 75 and 76 via which three motor windings 78, 79 and 80 of an electric motor 82 integrated into the hand-piece 14 can be supplied with current. Hereby, the coupling contact 66 is connected in electrically conductive manner to the line 74, the coupling contact 67 to the line 75. Moreover, the two coupling contacts 68 and 69 are connected in electrically conductive manner to the line 76.

For the purposes of mechanically coupling the two coupling devices 62 and 64, the first coupling device 62 comprises a first coupling element 84 and the second coupling device 64 a second coupling element 86. They can be brought into engagement with one another in a coupling position. The coupling system 60 is schematically illustrated in the coupling position in FIG. 7. The first coupling element 84 is preferably in the form of a coupling sleeve 88 into which the second coupling element 86 in the form of a coupling plug 90 can be inserted in a direction parallel to a longitudinal axis 92 of the coupling system 60.

The first coupling device 62 has a proximal end which is in the form of a cable protection sleeve 94 serving as a strain reliever from which a cable 96 consisting of three lines 74, 75 and 76 is led out. A substantially rotationally symmetrical bearing body 98 extends from the cable protection sleeve 94 in the distal direction and is surrounded by the coupling sleeve 88 extending in the distal direction. Commencing from the bearing body 98 and within the coupling sleeve 88, there extends a cylindrical socket body 100 which, in the interior thereof, comprises four plug sockets 102, 103, 104 and 105 that are formed from an electrically conductive material. The plug sockets 102, 103, 104 and 105 form the electrical coupling contacts 66, 67, 68 and 69. They are open in the distal direction and the longitudinal axes thereof are aligned in parallel with the longitudinal axis 92. Two peripheral annular grooves 110 and 112, which define locking recesses and are spaced from each other in the axial direction, are formed in an inner wall 108 of the coupling sleeve 88 and are spaced somewhat from a distal end 106 thereof. The annular groove 110 is spaced from the end 106 by approximately the same distance as a distal end 114 of the socket body 100.

Somewhat on the proximal side of the annular groove 110, the coupling sleeve 88 is provided with a boring 116 which is oriented transversely relative to the longitudinal axis 92 and into which there projects a short cylindrical pin 118 which forms a release member 120 and is arranged on a release lever 122 protruding perpendicularly therefrom. The release lever 122 is formed from an L-shaped leaf spring 124 which comprises a short arm 126 that is held on the bearing body 98 by means of a screw 128 having a longitudinal axis which extends in parallel with the longitudinal axis 92. A long arm 130 of the leaf spring 124 protrudes through a through passage 132 in the coupling sleeve 88 and extends substantially parallel to the longitudinal axis 92 outside of the coupling sleeve 88 in the distal direction. Commencing from a distal end of 134 of the long arm 130, there is an actuating projection 138 which is located on the outer surface 136 thereof. This projection protrudes through an elongate through passage 140 of a substantially elongate cuboidal guidance body 142. The guidance body 142 has a projection 144 pointing in the direction of the longitudinal axis 92 which engages at the proximal side thereof in the through passage 132 and abuts on an edge thereof at one side and against the arm 126 on the other side. It is likewise secured to the bearing body 98 by the screw 128. At the distal side thereof, the guidance body 142 is provided with a recess 146 which points in the proximal direction and in which the end 106 engages. Commencing from the end 106 and for the purposes of unambiguously positioning the guidance body 142 on the coupling sleeve 88, the latter is made somewhat thinner in the peripheral direction in correspondence with the width of the guidance body 142 thereby providing unambiguous positioning of the guidance body in the peripheral direction. A distal end of the guidance body 142 extending in parallel with the longitudinal axis 92 in the distal direction protrudes beyond the end 106 and forms a blocking member 148, the functioning of which will be described in more detail hereinbelow.

As is schematically illustrated in FIG. 3a, by the application of force to the actuating projection 138 in the direction of the arrow 150, i.e. transverse to the longitudinal axis 92 and directed towards it, the end of the release lever 122 pointing in the distal direction can be pivoted in the direction of the longitudinal axis 92 until a lower surface 152 of the arm 130 strikes an outer surface 154 of the coupling sleeve 88. The actuated position of the release member 120 is therefore illustrated in FIG. 3a, the unactuated position thereof in FIG. 2. Furthermore, the guidance body 142 comprises a locating nose 156 which projects from the inner wall 108 somewhat in the direction of the longitudinal axis 92. It serves for centring purposes when moving the two coupling devices 62 and 64 into engagement.

The construction of the second coupling device 62 is described in more detail in conjunction with FIGS. 4 and 5 hereinafter.

A rotationally symmetrical bearing body 158 simultaneously defines a distal end 160 of the second coupling device 64 which a housing 162 of the hand-piece 14 adjoins. Thereby, the coupling plug 90 projects in the proximal direction from the bearing body 158 and thus from the housing. It is not a one-piece body, but is in multipart form. A plug sleeve 164 is formed in one piece manner with the bearing body 158. This sleeve comprises a short section 166 having an outer diameter that is somewhat reduced in relation to a cylindrical inner section 168. At the proximal side thereof adjoining the section 166, there is a further cylindrical section 170 having an outer diameter which is again somewhat reduced in relation to that of the section 166. At the proximal side thereof adjoining the section 170, there is a further cylindrical section 172 which, in toto, takes up somewhat more than half the overall length of the plug sleeve 164. A last substantially cylindrical section 174 forms a ring flange 178 which extends up to the proximal end 176. This section is provided on the interior thereof with an annular groove 180.

On an outer surface thereof, the section 172 is provided with a flat recess 182 into which a locking body 184 is inserted. The latter is made of a resilient springy material and comprises a retaining section 186 which defines a distal end and extends over a peripheral angle of 180°. The internal curvature of the retaining section 186 is adapted to the section 170. For the purposes of unambiguously positioning the retaining section 186 on the plug sleeve 164, there is formed on the section 170 directly adjacent the section 166 a cuboidal nose 188 which engages in a corresponding recess 190 in the retaining section 186 oriented in the distal direction.

From the retaining section 186 and extending in the proximal direction, there is a holding member 192 which is provided with a slot 196 commencing from a proximal end 194. Thus, in practice, there are formed two springy resilient holding arms 198 which are symmetrical with respect to a mirror plane 92 containing the longitudinal axis 92. Furthermore, the holding member 192 is provided with two through holes 200 and 202 that are oriented transversely relative to the longitudinal axis 92. The through hole 202 is formed directly outgoing from the end 194 and is substantially semicircular. The through hole 200 is spaced by a distance 204 from the through hole 202.

The respective holding arms 198 are equipped in the peripheral direction with holding tabs 206 which point away from each other and which each carry a rotationally symmetrical locking projection 208 that points away from the longitudinal axis 92 in the radial direction. A diameter of the locking projections 208 corresponds approximately to a width 210 of the annular grooves 110 and 112. The recess 182 is formed and dimensioned in such a way that the holding arms 198 are pivotal somewhat in the direction of the longitudinal axis 92 upon the application of an appropriate force. The locking projections 208 thus form studs which are moveable in the radial direction.

A control element 212 partially abuts on an outer surface of the holding member 192 facing away from the longitudinal axis 92. The element comprises a holding section 214 which partially covers the holding section 186. For the purposes of unambiguously positioning the control element 212 relative to the bearing body 158, there is a narrow cuboidal nose 216 which is formed on the section 166 and which projects in the radial direction and engages in a corresponding recess 218 in the holding section 214. In like manner to the holding member 192, the control element 212 is mirror-symmetrical with respect to a mirror plane containing the longitudinal axis 92. It has two control arms 220 which project from the holding section 214 in the proximal direction and are substantially parallel to the longitudinal axis 92. These arms are separated from each other by a gap 222. The width 224 of the gap 222 in the peripheral direction is somewhat greater than a diameter 226 of the release member 120. Projecting from the mutually facing inner edges 228 of the control arms 220, there are two control projections 232 at the proximal end 230 of the control arms 220 which point towards one another and are separated from each other by a gap 234. Spaced therefrom at a distance 236 in the distal direction 228, there are two second control projections 238 which project from the inner edges towards one another and are separated from each other by a further gap 240. Moreover, the control element 212 has a U-shaped slot 242 which divides each control arm 220 into two substantially mutually parallel control arms 244 and 246. The distal ends of the control arms 244 carrying the control projections 232 and 238 are separated from each other by a further gap 248.

The special design of the control element 212 enables the ends 230 of the control arms 220 to be pivoted in the direction of the longitudinal axis 92 and then back again. Moreover, the ends 230 can be pivoted away from each other and back again in the peripheral direction in order to enlarge the gaps 234 and 240. Moreover, the distal ends 250 of the control arm 246 can be pivoted away from each other and back again in the peripheral direction in order to enlarge the gap 248.

Commencing from the end 176 thereof, a protective sleeve 252 extending in the distal direction surrounds the bearing body 158. This sleeve has a continuous lengthwise slot 254, parallel to which furthermore, there are two elongate holes 256. The widths of the elongate holes 256 are dimensioned in such a way that the locking projections 208 can engage through them. In essence therefore, an outer contour of the coupling plug 90 is determined by an envelope defined by the protective sleeve 252 beyond which the locking projections 208 project somewhat in the radial direction when in a basic position.

The bearing body 158 is provided with a blind hole 258 commencing from its end 176. Four contact pins 260, 261, 262 and 263 are arranged in the blind hole 258, said pins having a free end pointing in the proximal direction and are formed in correspondence with the plug sockets 102, 103, 104 and 105. The contact pins 260, 261, 262 and 263 form the coupling contacts 70, 71, 72 and 73.

As schematically illustrated in FIG. 16a, the coupling contact 70 is connected to the motor winding 79 in an electrically conductive manner. The motor winding 79 is connected to the motor windings 78 and 80 in a star configuration. Furthermore, the motor winding 78 is connected to the coupling contact 71 in electrically conductive manner. The motor winding 80 is on the one hand connected in electrically conductive manner to the coupling contact 72 and on the other to a resistance 264 which forms a coding element 266 for coding the type of hand-piece 14. A resistance value of the resistance 264 is unambiguously associated with the kind or type of the hand-piece 14 or corresponds thereto. In particular, the association can be determined by the type of electric motor 82 so that control of the electric motor 82 as adapted to the hand-piece 14 can be effected by the controller 12. The resistance 264 is connected in series between the motor winding 80 and the coupling contact 73.

The contact pins 261 and 262 are shorter than the contact pins 260 and 263. A spacing 268 between the free ends of the contact pins 261 and 262 on the one hand and 260 and 263 on the other parallel to the longitudinal axis 92 is somewhat greater than the spacing 270 of the annular grooves 110 and 112 from each other.

Furthermore, there is provided on the housing 162 a tool coupling device 272 for coupling a distal end of the hand-piece 14 in releasable manner to a working tool that is not illustrated in detail. It comprises a tool coupling member 274 which is displaceable somewhat towards the bearing body 158 in the direction of the arrow 276 for uncoupling the working tool. The tool coupling member 274 passes partially through the housing 162 and has a free end 278 which is oriented in the proximal direction.

The functioning of the coupling system 60 is described in more detail hereinafter in conjunction with FIGS. 7a to 13.

Commencing from the separated position illustrated in FIG. 2, the coupling devices 62 and 64 can be brought into engagement with one another so that they adopt a mechanical coupling position such as is schematically illustrated in FIG. 7a. It is irrelevant thereby as to whether the release member 120 adopts the actuated or the unactuated position. The release member 120 is illustrated in the actuated position in FIG. 7a. The pin 118 then protrudes beyond the inner wall 108 to such an extent that it slides on the inclined slide-edges 280 of the first control projections 232 pointing in the proximal direction and engages between them by enlarging the gap 234 and moves them away from each other. In this position which is referred to as the release position and is schematically illustrated in FIG. 7b, the spacing of the first control projections 232 is greater than it is in the driving position illustrated in FIG. 4 which the control element 212 adopts without external forces being effective thereon.

In addition, the first control projections 232 are arranged in such a manner that they cover the through hole 202 in the driving position and expose it in the release position. Consequently, the release member 120 cannot come into contact with the holding member 192 in the release position. In the basic position thereof, the holding arms 198 can thereby adopt a position in which they are sprung out to the maximum extent from the longitudinal axis 92. If the coupling plug 90 is inserted so far into the coupling axis 88 that the locking projections 208 are located at the level of the annular groove 110, the holding arms 198 spring away from the longitudinal axis 92 in the radial direction and the locking projections 208 engage in the annular groove 110. This becomes possible because, during the process of inserting the coupling plug 90, the locking projections 208 slide on the inner wall 108 and would be pivoted somewhat in the direction of the longitudinal axis 92.

The annular grooves 110 and 112 form first and second locking elements 282 and 284, the locking projections 208 third locking elements 286 of a locking device bearing the general reference symbol 288.

In the OFF position of the coupling system 60 illustrated in FIG. 7*a*, the contact pins 260 and 263 engage in the corresponding plug sockets 102 and 105. Consequently, an electrical circuit is closed in which the coupling contact 70 is connected in series with the motor winding 79, the motor winding 80, the resistance 264 and also the coupling contact 73. This is illustrated schematically in FIG. 16. In the OFF position, by applying a voltage to the lines 74 and 76 and by determining the current then flowing together with knowledge of the resistance values of the motor windings 79 and 80, a resistance value of the resistance 264 can be computed and, from the resistance value thereby determined, a conclusion can in turn be drawn as to the type of the electric motor 82. This determination can be effected automatically by appropriate configuration or programming of the controller 12.

The electric motor 82 can then be controlled by the controller 12 in a desired manner for setting a working tool into rotation by the electric motor 82 for example.

Furthermore, the coupling system 60 comprises a switching position securing device 290 for mechanically securing a switching device 292 comprised by the coupling system 60 and formed by the co-operation of the two coupling devices 62 and 64 in the described OFF position and also in an ON position in which each of the contact pins 260, 261, 262 and 263 engages in the respectively corresponding plug socket 102, 103, 104 or 105. The switching position securing device 290 comprises the locking device 288 which serves for mechanically locking the coupling devices 62 and 64 when adopting the coupling position in the described OFF position and also in the ON position of the switching device 292 which will be described later. Moreover, the switching position securing device 290 comprises a releasing device bearing the general reference symbol 294 for effecting the mechanical release of the locking device. The releasing device 294 serves for moving the locking elements 282 and 286 out of engagement from the OFF position into a switching position in which the coupling devices 62, 64 could be moved relative to each other in the axial direction. For this purpose, the releasing device 294 comprises the release member 120. In the coupling system 60 illustrated in the Figures, the release member 120 is configured to be moved indirectly into engagement or contact with the third locking element 286 for the purposes of transferring the locking device 288 both from the OFF position and from the ON position into the switching position.

When, as described above, the coupling plug 90 with an actuated release member 120 is inserted into the coupling sleeve 88, the release member 120 spreads the first control projections 232 whereby actuation of the holding member 192, as a result of which the two locking elements 286 would be fed out of the annular groove 110, is not possible. For this purpose, the release member 120 must first be released so that the control element 212 can change over from the release position into the driving position. The third locking elements 286, which are arranged or mounted on the holding member 192, are then moved away from the longitudinal axis 92 in the radial direction into the annular groove 110 due to the action of a biasing device 296. The biasing device 296 comprised by the locking device 288 serves for holding the locking elements 282 and 286 on the one hand and 284 and 286 on the other in the OFF position or in the ON position. The locking elements 282 and 286 or 284 and 286 can only be brought out of engagement against a biasing force exerted by the biasing device 296. The biasing device 296 comprises the holding arms 198 and hence the holding member 192 which is resiliently springy and, without a force being exerted by the release member 120, moves the locking elements 286 away from the longitudinal axis 92 or holds them in a position that is maximally remote from the longitudinal axis 92.

The control element 212 is provided in order to ensure that in the process of moving the coupling devices 62 and 64 into engagement with one another, the coupling system 60 will initially adopt the OFF position independently of whether the release member 120 is actuated or not. It is moveable from the driving position, in which the release member 120 is moveable by means of the control element 212 indirectly into contact or engagement with the third locking element 266 for the purposes of transferring the locking device 288 from the OFF position or from the ON position into the switching position, into the release position in which the release member 120 is moveable neither directly nor indirectly into contact or engagement with the third locking element 286 to a sufficient extent for transferring the locking device 288 from the OFF position or from the ON position into the switching position. This release position is schematically illustrated in FIGS. 7*a* and 7*b*. Due to the spreading of the control element 212 when the release member 120 engages between the first control projections 232, it is not then possible, if the release member 120 adopts the actuated position, to move the holding member 192 in the direction of the longitudinal axis 92 by the release member 120 in order to thereby move the locking elements 286 and 282 out of engagement. So as to enable the latter action to take place, the release member 120 must first be transferred into its unactuated position. This is simply done by means of an operator releasing the actuating projection 138 so that the release lever 122 can spring back into its starting position in which the release member 120 protrudes somewhat beyond an outer surface 136 of the guidance body 142.

As a result of the movement of the release member 120 out of the gap 234 between the first control projections 232, the latter spring back into their proximity position or driving position due to the resilient springy nature of the control arms 244. In this position, the first control projections 232 conceal the through hole 200. If the release member 120 is now actuated again, i.e. moved in the direction of the longitudinal axis 92, it initially strikes the two control projections as is schematically illustrated in FIG. 9, and carries along therewith the holding arms 198 in the course of a pivotal movement of the control arms 220 in the direction of the longitudinal axis 92, whereby the locking elements 286 are moved out of the annular groove 110. The coupling system 60 is now in the switching position. The two coupling devices 62 and 64 can now either be transferred back again into the separated position in which they are pulled apart, or they can be pushed together still further in order to transfer the switching device 292 from the OFF position into the ON position.

If, as schematically illustrated in FIGS. 10*a* and 10*b*, the coupling devices 62 and 64 are moved further towards one another, then, with an actuated release member 120, the holding member 192 springs radially outward as soon as the release member 120 engages in the region between the first control projections 232 and the second control projections 238. If the release member 120 is kept actuated and the coupling devices 62 and 64 are moved further towards one another, then the release member strikes the slide-edges 298 of the second control projections 238 which point in the proximal direction and pushes itself between them into the gap 240, whereby in turn, the control arms 220 are spread apart and the second control projections 238 are moved apart whilst simultaneously enlarging the spacing therebetween and thus too, the width of the gap 240. The control element 212 now again adopts the release position in which the release member 120 is located directly over the through hole 200 and thus cannot come into engagement with the holding member 192 and thus indirectly with the third locking elements 286. Exactly in the position in which the release member 120 engages in the gap 240, the locking elements 286 are located at the level of the annular groove 112 and thus, due to the biasing device 296, are brought into engagement with the second locking element 284. In other words, the coupling system 60 automatically latches itself in the ON position as soon as the locking projections 208 are located axially at the level of the annular groove 212.

The coupling contacts 67 and 71 on the one hand and also the coupling contacts 68 and 72 on the other are in engagement in the ON position. The ON position is schematically illustrated in FIG. 16c. In the ON position, the windings 78, 79 and 80 of the electric motor 82 can be energised in a desired manner by means of the controller 12 in order to set the electric motor 82 and a working tool possibly coupled thereto into rotation.

Moreover, the locking device 288 has yet another function. In the ON position of the coupling system 60 as schematically illustrated in FIG. 12a, the blocking member 148 forms a stop for the tool coupling member 274 and prevents a movement thereof in the proximal direction. If a working tool is coupled to the hand-piece 14 and the tool coupling member 274 is in its distal position, i.e. not withdrawn, the tool coupling device 272 adopts the tool coupling position. Consequently, withdrawal in the proximal direction into a tool separating position is only possible if the coupling system 60 is not in the ON position, i.e. the spacing between the blocking member 148 and a proximal end of the tool coupling member 274 is sufficiently large for the latter to be moved from the tool coupling position into the tool separating position. This security function of the coupling system 60 prevents an operator from inadvertently actuating the tool coupling member 274 when the coupling system 60 is in the ON position and can thereby prevent unwanted uncoupling or releasing of a working tool coupled to the hand-piece 14. If the coupling system 60 adopts the ON position, then initially it can only be transferred actively from the ON position into the switching position if the release member 120 has been transferred at least once into its unactuated position. This is schematically illustrated in FIGS. 12a and 12b. For unlocking purposes, i.e. moving the locking projections 208 and the annular groove 112 out of engagement, then the release member 120 must be moved again in the direction of the longitudinal axis 92. Due to the transferral of the release member 120 from the operated into the unactuated position, the second control projections 238 could be moved back towards one another again by the action of the control arms 220 forming a restoring device 300, whereby the gap 240 would be minimized. A movement of the release member 120 in the direction of the control element 212 which is now in the driving position as schematically illustrated in FIG. 12b permits it to be used quasi as a drive means for the holding member 192 so that, as the result of a pivotal movement of the second control projections 238 in the direction of the longitudinal axis 92, the holding arms 198 are likewise pivoted in the direction of the longitudinal axis 92, whereby the locking projections 208 and the annular groove 212 become disengaged. This is illustrated schematically in FIG. 13. The coupling devices 62 and 64 can now be pulled apart again.

Nevertheless, overshooting the OFF position is likewise not possible during the pulling-apart process as was already the case during the process of pushing the coupling devices 62 and 64 together. If the release member 120 is actuated during the process of pulling the coupling devices 62 and 64 apart, it initially comes into contact with the inclined slide-edges 302 of the first control projections 232 which point in the distal direction and spreads them apart again. As soon as the locking projections 208 are located at the level of the annular groove 110, the biasing device 296 causes them to latch together. In this way, the coupling devices 62 and 64 can be prevented from being unintentionally released from one another during the transition from the ON position into the OFF position. If, however, this is desirable, the release member 120 must firstly be transferred back again into the unactuated position. Due to the freeing of the gap 234, the first control projections 232 spring back again towards one another thereby adopting the driving position again, and enable the locking projections 208 and the annular groove 110 to disengage again as a result of a renewed actuation of the release member 120. The coupling system 60 can now be transferred either into its separated position or back again into the ON position.

Consequently, due to the special configuration of the coupling system 60, an electromechanical switching element in the form of the switching device 292 can be formed in a simple manner.

A slightly modified embodiment of the coupling system 60 is partially illustrated schematically in FIGS. 14 and 15. It differs from the coupling system 60 described above only by the shape of the locking projections 208. These are substantially in the form of a cuboid in the exemplary embodiment illustrated in FIGS. 14 and 15 in contrast to the rotationally symmetric design in the exemplary embodiment illustrated in FIGS. 2 to 13.

The coupling system is preferably made exclusively of materials which are suitable for a superheated steam sterilization process.

What is claimed is:

1. A surgical coupling system, comprising:
    a first surgical coupling device and a second surgical coupling device each having at least two electrical coupling contacts that are moveable mechanically into engagement with one another,
    the first and the second coupling device being completely separated from each other in a separated position and being mechanically in engagement with one another in a mechanical coupling position,
    in the coupling position, the first and second coupling devices being moveable relative to one another between an OFF position, in which at least one first electrical coupling contact of the first coupling device and at least one first electrical coupling contact of the second coupling device are out of engagement, and an ON position in which the at least one first electrical coupling contact of the first coupling device and the at least one first electrical coupling contact of the second coupling device are in electrically conductive contact or engagement, and
    a switching position securing device for mechanically securing the first and second coupling devices in the ON position and in the OFF position.

2. A surgical coupling system in accordance with claim 1, wherein:

the first and the second coupling device each comprise at least one second electrical coupling contact, and the second coupling contacts are in electrically conductive contact or engagement with one another in the OFF position and in the ON position.

3. A surgical coupling system in accordance with claim 1, wherein:
one of the two coupling devices comprises at least one first coupling element,
the other one of the two coupling devices comprises at least one second coupling element which is formed in correspondence with the at least one first coupling element, and
the at least one first and the at least one second coupling element are in engagement with one another in the coupling position.

4. A surgical coupling system in accordance with claim 1, wherein the switching position securing device comprises a locking device for mechanically locking the first and second coupling devices adopting the coupling position in the ON position and in the OFF position and a releasing device for mechanically releasing the locking device.

5. A surgical coupling system in accordance with claim 4, wherein:
the locking device comprises first and second locking elements and also a third locking element,
the first and second locking elements are arranged or formed on one of the two coupling devices,
the third locking element is arranged or formed on the other one of the two coupling devices, and
the first and the third locking element are in engagement in the ON position and the second and the third locking element are in engagement in the OFF position.

6. A surgical coupling system in accordance with claim 5, wherein the locking device comprises a biasing device for holding the locking elements in the ON position or in the OFF position.

7. A surgical coupling system in accordance with claim 5, wherein the first and the third locking element, and the second and the third locking element are arranged or formed such as to be moveable relative to each other in a radial direction with respect to a longitudinal axis of the coupling system for the process of being moved into and out of engagement.

8. A surgical coupling system in accordance with claim 5, wherein the releasing device is configured to move the first and third locking elements out of engagement from the ON position into a switching position in which the coupling devices are moveable relative to each other in an axial direction.

9. A surgical coupling system in accordance with claim 5, wherein the releasing device is configured to move the second and third locking elements out of engagement from the OFF position into the switching position.

10. A surgical coupling system in accordance with claim 5, wherein the releasing device comprises a movably mounted release member which is moveable from an unactuated position into an actuated position and/or vice versa.

11. A surgical coupling system in accordance with claim 10, wherein the release member is moveable directly or indirectly into engagement or contact with the third locking element to transfer the locking device from the ON position or from the OFF position into a switching position in which the coupling devices are moveable relative to each other in an axial direction.

12. A surgical coupling system in accordance with claim 11, wherein the releasing device comprises at least one mechanical control element which is moveable from a driving position, in which the release member is moveable directly or indirectly into contact or engagement with the third locking element by means of the control element to transfer the locking device from the ON position or from the OFF position into the switching position, into a release position in which the release member is moveable neither directly nor indirectly into contact or engagement with the third locking element to an extent sufficient for transferring the locking device from the ON position or from the OFF position into the switching position.

13. A surgical coupling system in accordance with claim 12, wherein the control element is moveable in a direction of a longitudinal axis of the coupling system on which the coupling device comprising the third locking element is arranged or formed.

14. A surgical coupling system in accordance with claim 12, wherein the releasing device is configured in such a manner that the release member in the actuated position transfers the control element from the driving position into the release position for preventing the release member being moveable directly or indirectly into contact or engagement with the third locking element to transfer the locking device from the ON position or from the OFF position into the switching position.

15. A surgical coupling system in accordance with claim 12, wherein the releasing device is configured in such a manner that the control element is transferable from the release position into the driving position only by transferring the release member from the actuated position into the unactuated position.

16. A surgical coupling system in accordance with claim 12, wherein the releasing device is configured in such a manner that only in the driving position is the release member moveable directly or indirectly into contact or engagement with the third locking element to transfer the locking device from the ON position or from the OFF position into the switching position.

17. A surgical coupling system in accordance with claim 12, wherein the control element comprises at least one first control projection that is associated with the first locking element and at least one second control projection that is associated with the second locking element and both of which are moveable transversely relative to a direction of movement of the release member to transfer the control element from the driving position into the release position and vice versa.

18. A surgical coupling system in accordance with claim 17, wherein there are provided two first and/or two second control projections which are spaced from each other by a greater distance in the release position than in the driving position.

19. A surgical coupling system in accordance with claim 18, wherein the first control projections and/or the second control projections are separated from each other by a slot in which the release member engages in the actuated position as a consequence of a movement of the two coupling devices towards one another or away from each other to forcibly move the control projections away from each other in opposite directions into the release position.

20. A surgical coupling system in accordance with claim 12, wherein the releasing device comprises a restoring device for automatically transferring the control element from the release position into the driving position as soon as the release member is transferred from the actuated position into the unactuated position.

21. A surgical coupling system in accordance with claim 1, further comprising an electrical supply line having a first and a second end, wherein:

the first coupling device is arranged or formed at the first end, and the second end is connected or connectable in releasable manner to a control and/or regulating device for the control and/or regulation of a surgical electric motor.

22. A surgical coupling system in accordance with claim 1, further comprising a surgical hand-piece having an electric motor for driving a surgical tool that is coupled or couplable to the hand-piece, which hand-piece has a proximal and a distal end, at which said proximal end the second coupling device is arranged or formed.

23. A surgical coupling system in accordance with claim 2, wherein the first electrical coupling contacts are shorter than the second electrical coupling contacts.

24. A surgical drive system, comprising:

at least one surgical hand-piece comprising a drive in the form of an electric motor, a control and/or regulating device for controlling and/or regulating the electric motor, at least one electrical supply line, the at least one electrical supply line comprises a first end that is connectable to the at least one hand-piece in releasable manner and a second end that is connected or connectable in releasable manner to the control and/or regulating device, a coupling system for electrical and mechanical connection of the hand-piece and the supply line, said coupling system comprising:

a first surgical coupling device and a second surgical coupling device each having at least two electrical coupling contacts that are moveable mechanically into engagement with one another, the first and the second coupling device being completely separated from each other in a separated position and being mechanically in engagement with one another in a mechanical coupling position, in the coupling position, the first and second coupling devices being moveable relative to one another between an OFF position, in which at least one first electrical coupling contact of the first coupling device and at least one first electrical coupling contact of the second coupling device are out of engagement, and an ON position in which the at least one first electrical coupling contact of the first coupling device and the at least one first electrical coupling contact of the second coupling device are in electrically conductive contact or engagement, and a switching position securing device for mechanically securing the first and second coupling devices in the ON position and in the OFF position.

\* \* \* \* \*